US012018044B2

(12) United States Patent
Berlanda Scorza et al.

(10) Patent No.: US 12,018,044 B2
(45) Date of Patent: *Jun. 25, 2024

(54) RNA PURIFICATION METHODS

(71) Applicant: GLAXOSMITHKLINE BIOLOGICALS SA, Rixensart (BE)

(72) Inventors: Francesco Berlanda Scorza, Holly Springs, NC (US); Yingxia Wen, Cambridge, MA (US); Andrew Geall, Cambridge, MA (US); Frederick Porter, Holly Springs, NC (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 316 days.

This patent is subject to a terminal disclaimer.

(21) Appl. No.: 17/157,150

(22) Filed: Jan. 25, 2021

(65) Prior Publication Data
US 2021/0214388 A1  Jul. 15, 2021

Related U.S. Application Data

(63) Continuation of application No. 14/775,760, filed as application No. PCT/EP2014/055014 on Mar. 13, 2014, now Pat. No. 11,155,572.

(60) Provisional application No. 61/799,705, filed on Mar. 15, 2013.

(51) Int. Cl.
*C12Q 1/68* (2018.01)
*B01D 15/36* (2006.01)
*B01D 15/38* (2006.01)
*B01D 61/14* (2006.01)
*C07H 1/06* (2006.01)
*C07H 21/00* (2006.01)
*C07H 21/02* (2006.01)
*C07H 21/04* (2006.01)
*C12N 15/10* (2006.01)

(52) U.S. Cl.
CPC ............ *C07H 21/02* (2013.01); *B01D 15/36* (2013.01); *B01D 15/38* (2013.01); *B01D 15/3847* (2013.01); *B01D 61/14* (2013.01); *C07H 1/06* (2013.01); *C07H 21/00* (2013.01); *C07H 21/04* (2013.01); *C12N 15/101* (2013.01); *C12N 15/1017* (2013.01); *B01D 2015/3838* (2013.01)

(58) Field of Classification Search
USPC .................. 435/6.1, 6.11, 91.1; 436/94, 501; 536/23.1, 24.3
See application file for complete search history.

(56) References Cited

U.S. PATENT DOCUMENTS 6,355,792 B1   3/2002   Michelsen et al.
8,075,780 B2  12/2011   Pearce
11,155,572 B2 * 10/2021  Berlanda Scorza ... B01D 15/38
2003/0203375 A1 10/2003 Kelly et al.
2008/0207487 A1  8/2008 DeFrees et al.
2013/0175164 A1  7/2013 Smith et al.
2013/0189757 A1  7/2013 Legault
2016/0040154 A1  2/2016 Heartlein et al.

FOREIGN PATENT DOCUMENTS

WO    WO 92/04970 A1    4/1992
WO    WO 98/05673 A1    2/1998
WO    WO 98/30685 A2    7/1998
WO    WO 2012/077080 A1 6/2012

OTHER PUBLICATIONS

GE Healthcare Life Sciences launches Capto™ Core 700 Chromatography Medium for Viruses and Other Large Biomolecules. News from pharmaceuticalonline, published on Apr. 3, 2012.*
Beckert et al., Synthesis of RNA by In Vitro Transcription. RNA Methods and Protocols, 703, 29-41, 2010.*
"T7 RNA polymerase" from Wikipedia. Printed on Mar. 11, 2023.*
"Capto™ Core 700" GE Healthcare Life Sciences (2012), Data File 28-9983-07 AA, pp. 1-4.
Adielsson et al., "New core bead chromatography medium enables group separation and high productivity purification of large biomolecules," Jul. 15, 2012. Retrieved from the Internet: URL:http://. processdevelopmentforum.com/ppts/posters/CaptoCore Updated Aug. 6 Final.pdf [retrieved on May 26, 2014].
Andrews-Pfannkoch et al. "Hydroxyapatite-mediated separation of double-stranded DNA, single-stranded DNA, and RNA genomes from natural viral assemblages," Applied and Environmental Microbiology (Aug. 2010), vol. 76, No. 15, pp. 5039-5045.
Azarani and Heckler, "RNA analysis by ion-pair reversed-phase high performance liquid chromatography," Nucleic Acids Research (2001), vol. 29, No. 2, e7, 9 pages.
High Screen Capto Core 700 multimodal chromatography resin of GE Healthcare Life Sciences. Printed on Mar. 30, 2020.
Cross-flow filtration from Wikipedia, the free encyclopedia. Printed on Mar. 30, 2020.
Draper, "A Guide to Ions and RNA Structure," RNA (2004), vol. 10, pp. 335-343.
Fernandez et al., "Cross flow filtration of RNA extracts by hollow fiber membrane," ACTA Biotechnol. (1992), vol. 12, pp. 49-56.

(Continued)

*Primary Examiner* — Frank W Lu
(74) *Attorney, Agent, or Firm* — Birch, Stewart, Kolasch & Birch, LLP

(57) ABSTRACT

Methods for purifying RNA from a sample, comprising one or more steps of tangential flow filtration, hydroxyapatite chromatography, core bead flow-through chromatography, or any combinations thereof. These techniques are useful individually, but show very high efficiency when used in combination, or when performed in particular orders. The methods can purify RNA in a highly efficient manner without unduly compromising potency or stability, to provide compositions in which RNA is substantially cleared of contaminants. Moreover, they can be performed without the need for organic solvents.

38 Claims, 15 Drawing Sheets

(56) References Cited

OTHER PUBLICATIONS

Vandernoot et al., "cDNA normalization by hydroxyapatite chromatography to enrich trnascriptome diversity in RNA-seq applications," Bio Techniques (Dec. 2012), vol. 53, pp. 373-380.

Vomelova et al., "Methods of RNA Purification. All Ways (Should) Lead to Rome," Folia Biologica (Prague) (2009), vol. 55, No. 6, pp. 243-251.

* cited by examiner

HOFMEISTER SERIES

Kosmotropic ←→ chaotropic

Cations
NH$_4^+$  K$^+$  Na$^+$  Li$^+$  Mg$^{2+}$  Ca$^{2+}$  guanidinium$^+$

Anions
SO$_4^{2-}$  HPO$_4^{2-}$  acetate$^-$  citrate$^-$  Cl$^-$  NO$_3^-$  ClO$_3^-$  I$^-$  ClO$_4^-$  SCN$^-$ ↑ surface tension
harder to make cavity
↓ solubility hydrocarbons
Salt out (aggregate)
↓ protein denaturation
↑ protein stability ↓ surface tension
easier to make cavity
↑ solubility hydrocarbons
Salt in (solubilize)
↑ protein denaturation
↓ protein stability

FIG. 2A

FIG. 6A 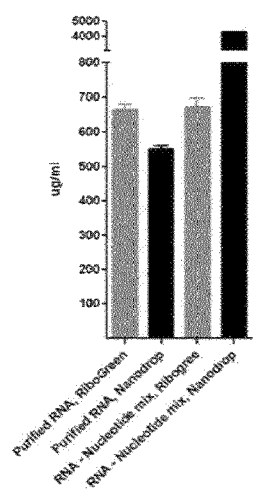 FIG. 6B 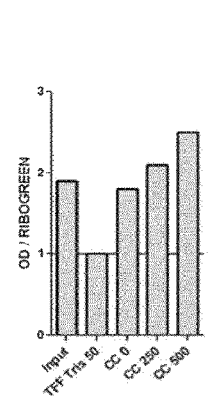 FIG. 6C 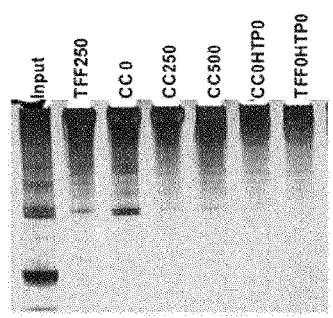
FIG. 6D

RNA PURIFICATION METHODS

CROSS-REFERENCE TO RELATED APPLICATIONS

The present application is a 37 C.F.R. § 1.53(b) continuation of U.S. application Ser. No. 14/775,760 filed Sep. 14, 2015 (now U.S. Pat. No. 11,155,572), which is the National Phase of PCT International Application No. PCT/EP2014/055014, filed on Mar. 13, 2014, which claims priority under 35 U.S.C. § 119(e) to U.S. Provisional Application No. 61/799,705, filed on Mar. 15, 2013, all of which are hereby expressly incorporated by reference in their entirety into the present application.

TECHNICAL FIELD

This invention is in the field of RNA purification, and in particular methods for the large-scale purification and formulation of large RNA from complex samples such as samples obtained after in vitro transcription of RNA, for pharmaceutical use, for example for use in immunising animals.

BACKGROUND ART

RNA is emerging as an innovative candidate for a variety of pharmaceutical applications, but efficient purification is continuing to be a challenge. This is partly due to the different types and combinations of undesired contaminants in a sample that need to be separated from a desired RNA species to obtain a pure RNA sample. Such contaminants are typically components and by-products of any upstream processes, for example RNA manufacture. Where in vitro transcription is used to manufacture large RNA, following successful transcription the sample typically contains the desired RNA species alongside various contaminants such as undesired RNA species, proteins, DNA or fragments thereof, pyrophosphates and free nucleotides.

Commercial downstream applications (e.g. formulation and use as a pharmaceutical composition and/or vaccine) pose further constrains on any purification method for large RNA requiring (i) a high degree of purity while retaining RNA stability and functionality; (ii) compatibility with any formulation requirements of the RNA for in vivo delivery; and (iii) compliance with good manufacturing practices. Furthermore, in order to facilitate industrial applications, any RNA purification method must enable consistent, cost- and time-efficient operation (e.g. quick, easy, reproducible, high yield purification on a large scale).

Methods for the purification of large RNA are known in the art. Pascolo et al. (2006) describes a method for the purification of mRNA from an in vitro transcription reaction sample in analytical scale (purification of 25 µg RNA in 20 µl sample volume). The method involves DNase treatment followed by precipitation of the longer mRNA with lithium chloride. However, the authors report that this method does not provide RNA of high purity, as it does not completely remove contaminants such as DNA and protein. Furthermore, the method involves the use of organic solvents and is laborious and time-consuming, involving as many as 36 steps requiring extensive manual sample handling at different conditions, including at least one overnight incubation step. Therefore, while this procedure may satisfy requirements for research and laboratory-scale RNA purification, it suffers from a low degree of RNA purity, reproducibility and is unsuitable for purification of pharmaceutical-grade RNA on a commercial scale for implementation in an industrial process.

WO2008/077592 discloses a method for purifying large RNA on a preparative scale with ion-pairing reverse phase HPLC using a porous reversed stationary phase. It is reported that a particular advantage of using the specified porous stationary phase is that excessively high pressures can be avoided, facilitating a preparative purification of RNA. However, the method involves the use of harsh organic solvents (e.g. acetonitrile) and high temperatures (78° C.) for the separation column, and a low temperature (12° C.) for the sampler. The nature of the contaminant(s) that can be successfully separated from a desired RNA using the method is not exemplified, including any requirements for preceding steps such as DNase treatment Additionally, chromatographic separation of RNA based on ion-pairing reverse phase HPLC or ion exchange resin are based on the molecule's total charge and may be effective for purification of RNA molecules of up to about 4,000-5,000 bases. However, the purification of larger RNA molecules suffers from size exclusion effects and poor recovery. Furthermore, it relies on elution of RNA using organic solvents, but these should ideally be avoided due to potential safety concerns about residues, high purchase costs, their environmental impact, and potential detrimental effects on RNA stability and potency.

Thus there remains a need for further and improved RNA purification methods, and in particular for those that allow cost- and time-efficient purification of large RNAs at an industrial scale with high yield and pharmaceutical-grade purity while retaining the stability, biological potency and functionality of the RNA. There is a particular need for such methods where the starting sample is a complex biological sample such as those obtained after in vitro transcription of large RNA.

DISCLOSURE OF THE INVENTION

To address these needs, the invention provides a method for purifying RNA from a sample, comprising one or more steps of tangential flow filtration, hydroxyapatite chromatography, core bead flow-through chromatography, or any combinations thereof. These techniques are useful individually, but show very high efficiency when used in combination, or when performed in particular orders. The methods can purify RNA in a highly efficient manner without unduly compromising potency or stability, to provide compositions in which RNA is substantially cleared of contaminants. Moreover, they can be performed without the need for organic solvents, and it is preferred that methods of the invention take place in aqueous conditions. A further advantage of the invention is that uses components which are essentially disposable, meaning that they can be prepared in thoroughly-cleaned form (in particular, RNase-free form), used only once, and then discarded, so that carry-through run-to-run contamination can be avoided, which is particularly useful when avoiding RNase contamination. The methods are also very quick.

In one embodiment, the invention provides a method for purifying RNA from a sample, wherein the method comprises one or more steps of tangential flow filtration.

In another embodiment, the invention provides a method for purifying RNA from a sample, wherein the method comprises one or more steps of hydroxyapatite chromatography.

In another embodiment, the invention provides a method for purifying RNA from a sample, wherein the method comprises one or more steps of core bead flow-through chromatography.

In a useful embodiment, the method comprises a step of tangential flow filtration and a step of hydroxyapatite chromatography. The step of tangential flow filtration preferably precedes the step of hydroxyapatite chromatography.

In another useful embodiment, the method comprises a step of core bead flow-through chromatography and a step of hydroxyapatite chromatography. The step of core bead flow-through chromatography ideally precedes the step of hydroxyapatite chromatography.

In any of the foregoing embodiments, the recited steps for RNA purification may be followed by one or more steps of buffer exchange e.g. comprising tangential flow filtration.

Thus the invention provides a method for the purification and formulation of RNA from a sample, wherein the method comprises one or more steps of RNA purification and one or more steps of buffer exchange. Preferably, the at least one step of buffer exchange comprises tangential flow filtration.

In one embodiment, the invention provides a method for the purification and formulation of RNA comprising two separate steps of tangential flow filtration. Preferably, a first buffer is used in a first step of tangential flow filtration and a second different buffer is used in a second step of tangential flow filtration. The first buffer and the second buffer are usually based on two different buffer salts. For example, the first buffer may be a Tris-based buffer whereas the second buffer may be a citrate buffer. Preferably, the first buffer is a purification buffer and the second buffer is a formulation buffer. More preferably, the purification buffer comprises a salt at a concentration of between 50-500 mM e.g. 250 mM.

For example, the purification buffer may comprise a salt at a concentration of between 0-500 mM, such as about 10 mM, about 20 mM, about 25 mM, about 50 mM, about 100 mM, about 150 mM, about 200 mM, about 250 mM, about 300 mM, about 350 mM, about 400 mM, about 450 mM, about 500 mM, from about 10 mM to about 500 mM, from about 10 mM to about 400 mM, from about 10 mM to about 300 mM, from about 10 mM to about 250 mM, from about 20 mM to about 500 mM, from about 20 mM to about 400 mM, from about 20 mM to about 300 mM, from about 20 mM to about 250 mM, from about 30 mM to about 500 mM, from about 30 mM to about 400 mM, from about 30 mM to about 300 mM, from about 30 mM to about 250 mM, from about 40 mM to about 500 mM, from about 40 mM to about 400 mM, from about 40 mM to about 300 mM, from about 40 mM to about 250 mM, from about 50 mM to about 500 mM, from about 50 mM to about 400 mM, from about 50 mM to about 300 mM, or from about 50 mM to about 250 mM, etc.

In another embodiment, the invention provides a method for the purification and formulation of RNA comprising a step of core bead flow-through chromatography, followed by a step of tangential flow filtration. In a preferred embodiment, a first buffer is used in the step of core bead flow-through chromatography and a second different buffer is used in the step of tangential flow filtration. Preferably, the first buffer is a purification buffer and the second buffer is a different formulation buffer. More preferably, the purification buffer comprises a salt, such as potassium chloride or sodium chloride. Most preferably, the purification buffer comprises potassium chloride at a concentration of between 100-500 mM e.g. 250 mM.

For example, the purification buffer may comprise potassium chloride at a concentration of between 0-500 mM, such as about 50 mM, about 75 mM, about 100 mM, about 150 mM, about 200 mM, about 250 mM, about 300 mM, about 350 mM, about 400 mM, about 450 mM, about 500 mM, from about 50 mM to about 500 mM, from about 50 mM to about 400 mM, from about 50 mM to about 300 mM, from about 50 mM to about 250 mM, from about 75 mM to about 500 mM, from about 75 mM to about 400 mM, from about 75 mM to about 300 mM, from about 75 mM to about 250 mM, from about 100 mM to about 500 mM, from about 100 mM to about 400 mM, from about 100 mM to about 300 mM, or from about 100 mM to about 250 mM, etc.

In another embodiment, the invention provides a method for the purification and formulation of RNA comprising a first step of tangential flow filtration, then a second step of hydroxyapatite chromatography, then a third step of tangential flow filtration. In a preferred embodiment, a first buffer is used in the first step of tangential flow filtration, a second different buffer is used in the second step of hydroxyapatite chromatography and a third different buffer is used in the third step of tangential flow filtration. Preferably, the first and second buffers are purification buffers and the third buffer is a different formulation buffer. Preferably, the first buffer is free from sodium chloride and/or potassium chloride. Most preferably, in an additional step, sodium chloride and/or potassium chloride is added to the RNA-containing sample at a final concentration of between 100-500 mM, e.g. 250 mM or 500 mM, after the first step of tangential flow filtration and before the second step of hydroxyapatite chromatography.

For example, sodium chloride and/or potassium chloride may be added to the RNA-containing sample at a final concentration of between 0-500 mM, such as about 50 mM, about 75 mM, about 100 mM, about 150 mM, about 200 mM, about 250 mM, about 300 mM, about 350 mM, about 400 mM, about 450 mM, about 500 mM, from about 50 mM to about 500 mM, from about 50 mM to about 400 mM, from about 50 mM to about 300 mM, from about 50 mM to about 250 mM, from about 75 mM to about 500 mM, from about 75 mM to about 400 mM, from about 75 mM to about 300 mM, from about 75 mM to about 250 mM, from about 100 mM to about 500 mM, from about 100 mM to about 400 mM, from about 100 mM to about 300 mM, or from about 100 mM to about 250 mM, etc.

In another embodiment, the invention provides a method for the purification and formulation of RNA comprising a first step of core bead flow-through chromatography, then a second step of hydroxyapatite chromatography, then a third step of tangential flow filtration. In a preferred embodiment, a first buffer is used in the first step of core bead flow-through chromatography, a second different buffer is used in the second step of hydroxyapatite chromatography and a third different buffer is used in the third step of tangential flow filtration. Preferably, the first and second buffer is a purification buffer and the third buffer is a different formulation buffer. Preferably, the first buffer is free from sodium chloride and/or potassium chloride. Most preferably, in an additional step, sodium chloride and/or potassium chloride is added to the RNA-containing sample at a final concentration of between 100-500 mM, e.g. 250 mM or 500 mM, after the first step of core bead flow-through chromatography and before the second step of hydroxyapatite chromatography.

For example, sodium chloride and/or potassium chloride may be added to the RNA-containing sample at a final concentration of between 0-500 mM, such as about 50 mM, about 75 mM, about 100 mM, about 150 mM, about 200 mM, about 250 mM, about 300 mM, about 350 mM, about 400 mM, about 450 mM, about 500 mM, from about 50 mM to about 500 mM, from about 50 mM to about 400 mM, from about 50 mM to about 300 mM, from about 50 mM to about 250 mM, from about 75 mM to about 500 mM, from about 75 mM to about 400 mM, from about 75 mM to about 300 mM, from about 75 mM to about 250 mM, from about 100 mM to about 500 mM, from about 100 mM to about 400 mM, from about 100 mM to about 300 mM, or from about 100 mM to about 250 mM, etc.

The invention also provides a method for purifying RNA from a sample (such as the product of an in vitro transcription reaction), wherein the RNA is purified to at least 99% purity (e.g. ≥99.5%, ≥99.9%, or even ≥99.95%) in less than 12 hours (e.g. <8 hours, <6 hours, <4 hours, or <2 hours).

In the methods of the invention, steps will generally involve discarding materials which do not contain RNA (or which do not contain the desired RNA species) while maintaining materials which contain RNA (or the desired RNA species). Thus, where a technique splits a starting material into fractions, desired fractions will be retained while undesired fractions can be discarded; similarly, if a technique retains undesired materials but lets desired RNA flow through, the flow through will be retained.

The RNA

According to the invention, a desired RNA is purified from an RNA-containing sample. The desired RNA of the invention can be double-stranded but is preferably single-stranded. Where the RNA is single-stranded, such as mRNA or a self-replicating RNA replicon, it typically encodes one or more proteins, and at least one of these is usefully an immunogen as discussed below but can also be any non-immunogenic therapeutic or prophylactic protein of interest (e.g. as a component of a gene therapy medicament). The desired RNA of the invention can be circular, but is preferably linear.

The RNA can be (—)-stranded, but is preferably is (+)-stranded, such that it can be translated by cells without needing any intervening replication steps such as reverse transcription. Preferred +-stranded RNAs are self-replicating, as described below. Preferably, the RNA is not a natural viral RNA.

The RNA may be a small, medium, or large RNA. The number of nucleotides per strand of a small RNA is from 10-30 (e.g. siRNAs). A medium RNA contains between 30-2000 nucleotides per strand (e.g. non-self-replicating mRNAs). A large RNA contains at least 2,000 nucleotides per strand e.g. at least 2,500, at least 3,000, at least 4,000, at least 5,000, at least 6,000, at least 7,000, at least 8,000, at least 9,000, or at least 10,000 nucleotides per strand (e.g. self-replicating RNAs as described below). The molecular mass of a single-stranded RNA molecule in g/mol (or Dalton) can be approximated using the formula: molecular mass=(number of RNA nucleotides)×340 g/mol.

As discussed in WO2011/005799, an RNA (particularly a self-replicating RNA) can include, in addition to any 5' cap structure, one or more nucleotides having a modified nucleobase. For instance, a RNA can include one or more modified pyrimidine nucleobases, such as pseudouridine and/or 5-methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7'-methylguanosine). In other embodiments, the RNA may include a 5' cap comprising a 7'-methylguanosine, and the first 1, 2 or 3 5' ribonucleotides may be methylated at the 2' position of the ribose.

A RNA used with the invention ideally includes only phosphodiester linkages between nucleosides, but in some embodiments it can contain phosphoramidate, phosphorothioate, and/or methylphosphonate linkages.

The invention is particularly suitable for purifying self-replicating RNAs. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded protein of interest (e.g. an immunogen), or may be transcribed to provide further transcripts with the same sense as the delivered RNA which are translated to provide in situ expression of a protein (e.g. an immunogen). The overall results of this sequence of transcriptions is a huge amplification in the number of the introduced replicon RNAs and so the encoded immunogen becomes a major polypeptide product of the cells. Suitable self-replicating RNAs are disclosed in WO2012/006369 and WO2013/006838.

One suitable system for achieving self-replication is to use an alphavirus-based RNA replicon. These +-stranded replicons are translated after delivery to a cell to give of a replicase (or replicase-transcriptase). The replicase is translated as a polyprotein which auto-cleaves to provide a replication complex which creates genomic --strand copies of the +-strand delivered RNA. These --strand transcripts can themselves be transcribed to give further copies of the +-stranded parent RNA and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a venezuelan equine encephalitis virus, etc. Mutant or wild-type viruses sequences can be used e.g. the attenuated TC83 mutant of VEEV has been used in replicons (WO2005/113782).

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, it is preferred that a self-replicating RNA molecule of the invention does not encode alphavirus structural proteins. Thus a preferred self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an immunogen. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicas e.

Self-replicating RNA molecules can have various lengths but they are typically 5000-25000 nucleotides long e.g. 8000-15000 nucleotides, or 9000-12000 nucleotides.

A RNA molecule useful with the invention may have a 5' cap. This cap can enhance in vivo translation of the RNA. The cap can be a natural or non-natural cap, and is generally attached to the RNA's 5'-terminal nucleotide by a 5' to 5' triphosphate linkage. Various cap structures are known e.g. 7-methylguanosine (m7G), 3'-O-Me-m7G or "ARCA" (anti reverse cap analog), m2,2,7G, unmethylated cap analogs, etc.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly-A tail. It may also include a poly-A polymerase recognition sequence (e.g. AAUAAA) near its 3' end.

In one embodiment, a method of the invention is used to purify a modified mRNA; in another embodiment, a method of the invention is used to purify an unmodified mRNA;

The RNA-Containing Sample

According to the invention, a desired RNA is purified from an RNA-containing sample. The composition of the sample will largely depend on the source of the RNA and any preceding purification steps. The methods of the invention are particularly useful for purification of a desired RNA from in vitro transcription (NT) sources. In these embodiments, the sample contains a desired RNA species and typically contaminants, including non-desired RNA, DNA (e.g. template DNA from NT), proteins (e.g. RNA polymerase, capping enzyme, DNase, RNase inhibitor), pyrophosphates and/or free nucleotides. Free nucleotides are found in NT mixtures either as un-reacted RNA precursors (e.g. ribonucleoside triphosphate) or as degradation products from DNA digestion (e.g. deoxynucleoside monophosphate). A typical buffer for IVT reactions is a Tris-based buffer, for example 50 mM Tris pH 8.0. A particular advantage of using NT is that a large excess of the desired RNA species is produced in a controlled reaction and that modified bases can easily be introduced into the RNA.

Thus a method of the invention may include a prepurification step of RNA manufacture by NT. Thus the invention provides a method for preparing a purified RNA, comprising steps of: (i) performing in vitro transcription to provide a sample comprising RNA; and (ii) purifying the RNA from the sample, comprising one or more steps of tangential flow filtration, hydroxyapatite chromatography, core bead flow-through chromatography, or any combinations thereof.

IVT produces RNA from a DNA template in a cell-free, controlled biochemical reaction typically including enzymes (e.g. RNA polymerase, and usually capping enzymes), RNA precursors (e.g. ribonucleoside triphosphate), DNA template, reducing agents (e.g. DTT), and a suitable buffer. Following IVT the DNA template should be removed to avoid its presence in the final product, and thus it can be digested (e.g. using DNase) or removed. Where the RNA purification method includes tangential flow filtration or core bead chromatography, it is preferred to remove DNA prior to purification, for example using DNase. In contrast, where the method uses hydroxyapatite chromatography the DNA can be removed without needing DNase treatment, although a step of DNase treatment can still be used if desired.

However, the invention is not limited to RNA from in vitro transcription reactions and in some embodiments RNA is manufactured using in vivo (cell-based) transcription, chemical synthesis, or synthetic genomics approaches.

Methods of the invention are also useful for the purification of RNA from an RNA-containing sample where the sample is an RNA virus extract, an RNA-containing cell extract (e.g. derived from animal, plant or bacterial cells), or an RNA-containing environmental sample or extracts thereof.

Purification of RNA from an RNA-Containing Sample

RNA purification is used to remove impurities from compositions comprising a particular RNA of interest. Different purification steps can be used to isolate the RNA of interest from non-RNA components of the composition (e.g. DNA and proteins), as well as from other contaminant RNA.

Methods of the invention use one or more of three techniques: tangential flow filtration; hydroxyapatite chromatography; and/or core bead flow-through chromatography. These methods can all be performed under aqueous conditions, so methods of the invention do not require the use of organic solvents, and are ideally performed without the use of organic solvents, in particular without the use of organic solvents that may be toxic when administered to humans as part of a pharmaceutical composition and/or which may adversely impact on the stability of large RNAs. Methods of the invention are therefore ideally performed without the use of acetonitrile, chloroform, phenol and/or methanol. Ideally, they can be performed without using any organic solvents.

Methods of the invention can conveniently be performed at room temperature.

Tangential Flow Filtration (TFF)

According to the invention, tangential flow filtration (TFF) may be used to purify a RNA of interest by removing lower molecular weight species. Thus a method of the invention can comprise one or more steps of TFF. TFF is particularly useful for the purification of large RNA species. The inventors have shown that high yield (at least 90-95%) and purity (at least 90-99.9%) can be achieved using TFF for RNA purification, while retaining the stability and potency of the purified RNA. Usefully, TFF also permits buffer exchange (dialysis) at the same time as purification (or TFF can be used with purified RNA as a separate buffer exchange step e.g. to change to a final formulation buffer. TFF is easy to operate, time-efficient (only about 70 minutes for both RNA purification and buffer exchange) and prevents contamination (e.g. with RNAse) due to the ability to operate as a closed system. TFF is particularly useful for the removal of free nucleotides from an NT mixture.

TFF involves passing a liquid containing the sample tangentially across a filter membrane. Thus TFF contrasts with dead-end filtration, in which sample is passed through a membrane rather than tangentially to it. In TFF the sample side is typically held at a positive pressure relative to the filtrate side. As the liquid flows over the filter, components therein can pass through the membrane into the filtrate. Where an IVT reaction sample is used, ribonucleoside triphosphates, small nucleic acid fragments such as digested template DNA, and/or other undesired components are typically removed in the filtrate whereas long RNA is recovered from the retentate. Many TFF systems are commercially available (e.g. using hollow fibres such as those available from GE Healthcare and Spectrum Labs). The molecular weight cut-off (MWCO) of a TFF membrane determines which solutes can pass through the membrane (i.e. into the filtrate) and which are retained (i.e. in the retentate). The MWCO of a TFF filter used with the invention will be selected such that substantially all of the solutes of interest (i.e. desired RNA species) remains in the retentate, whereas undesired components pass into the filtrate. The retentate may be re-circulated to the feed reservoir to be re-filtered in additional cycles. Compared to dead-end filtration, the retentate is washed away during the filtration process, minimising the clogging of the membrane which is known in the art as "membrane fouling", maintaining a high, steady filtration rate across the membrane, and increasing the length of time the process can be continuously operated.

Parameters for operating TFF according to the invention will be selected such that impurities can permeate the filter membrane whereas the RNA of interest is retained, without significantly affecting RNA integrity and/or potency.

The average pore size of a filter membrane is referred to in the art as "membrane pore size". Membrane pore size is usually stated in kDa and refers to the average molecular mass of the smallest particle or macromolecule the membrane is likely to retain. Alternatively, membrane pore size can be stated in μm and refers to the diameter of the smallest particle the membrane is likely to retain. The diameter is proportional to the molecular mass for molecules of a similar shape (e.g. spherical molecules). For example, a membrane pore size of 500 kDa is equivalent to a membrane pore size of approximately 0.02 μm for a spherical molecule.

The inventors have found that a membrane pore size of between 250 and 1000 kDa is useful when purifying large RNA e.g. between 250 and 750 kDa, or preferably between 400 and 600 kDa. A membrane having a pore size of about 500 kDa is particularly preferred. Preferably, the membrane pore size is selected such that the ratio of the size of the RNA molecule of interest to the membrane pore size is at least 1.5:1 (e.g. at least 2:1, at least 3:1, at least 4:1, at least 5:1 or at least 6:1) and/or that the ratio of the size of the largest non-RNA impurity to the membrane pore size is at least 1:1.5 (e.g. at least 1:2, at least 1:3, at least 1:4, at least 1:5 or at least 1:6).

Where a sample comprises a desired RNA and a non-desired RNA species of a different size, the method may include two or more steps of tangential flow filtration, wherein each step uses a different membrane pore size such that in one step smaller molecules than the RNA of interest are removed and the RNA-containing retentate fraction is retained, and in one or more additional steps larger molecules than the RNA of interest are removed and the RNA of interest is recovered from the filtrate. Such methods may be combined with hydroxyapatite chromatography and core bead flow-through chromatography as described below. Thus in one embodiment, the invention provides a method for purifying RNA from a sample, wherein the method comprises a first step of tangential flow filtration using a first membrane, optionally followed by (a) further step(s) of core bead flow-through chromatography and/or hydroxyapatite chromatography, followed by a second step of tangential flow filtration using a second membrane, wherein the first and second membranes have different pore sizes such that the first membrane retains the RNA of interest in the retentate and the second membrane permits the passage of the RNA of interest through the pores of the membrane into the filtrate and retains impurities in the retentate.

TFF may be carried out using any suitable filter membrane. The inventors have found that a hollow fibre filter is particularly advantageous. A hollow fibre filter typically comprises a multitude (bundle) of hollow, open-ended tubes (fibres), through which the liquid containing the sample is passed from the feed side to the retentate side. The walls of the tubes are composed of a membrane (the filter membrane), which typically has a three-dimensional internal structure of interconnected cavities (pores). Common filter membrane polymers that can be used in this invention are polysulfone (PS), polyethersulfone (PES). PES may be modified (mPES) to have increased hydrophilicity and to have higher permeate flux rates than un-modified PES. Several different methods are known to transform hydrophobic PES membranes into hydrophilic PES membranes. The inventors have found that hydrophilic membranes and particularly modified polyethersulfone (mPES) membranes are particularly advantageous for RNA purification.

TFF membranes may vary according to their effective surface area. The effective membrane surface area is typically stated in $cm^2$ and refers to the total surface of the filter membrane that is exposed to the sample. The effective surface area for hollow fibre membranes depends on the average diameter and effective length of the fibres and the total number of fibres. The inventors have found that the effective membrane area can influence the operation time of the TFF method and the efficiency of RNA purification and buffer exchange. Processing parameters determined for small-scale volumes can be used for larger volumes by maintaining the effective length of the filter and increasing the effective membrane area (e.g. by increasing the average fibre diameter and/or the total number of fibres).

A TFF method may vary according to the transmembrane pressure that is applied during the process. Transmembrane pressure is the average pressure differential between the feed side and the filtrate side of the filter membrane. Ideally, the transmembrane pressure is chosen so that a high flux of the fluid across the membrane is achieved while maintaining efficient separation of the RNA of interest from any impurities and avoiding the formation of a gel layer on the surface of the filter membrane. The inventors have found that a transmembrane pressure between 1 psi (6895 Pa) and 5 psi (34475 Pa) is preferred. Ideally, the transmembrane pressure is set to about 2 psi (13790 Pa).

A TFF method may vary according to the shear rate, or also known in the art as the retentate velocity. The shear rate is typically stated in reciprocal seconds ($s^{-1}$) and can be calculated according to formulae known in the art. Ideally, the shear rate is chosen so that a high flux of the fluid through the filter is achieved while maintaining RNA integrity and avoiding the formation of a gel layer on the surface of the filter membrane. The inventors have found that a shear rate between about 500-5000 $s^{-1}$ is preferred. More preferably, a shear rate of about 800 $s^{-1}$ is used.

For example, a shear rate of about 500 $s^{-1}$, about 600 $s^{-1}$, about 700 $s^{-1}$, about 800 $s^{-1}$, about 900 $s^{-1}$, about 1000 $s^{-1}$, about 1100 $s^{-1}$, about 1200 $s^{-1}$, about 1300 $s^{-1}$, about 1400 $s^{-1}$, about 1500 $s^{-1}$, about 1600 $s^{-1}$, about 1700 $s^{-1}$, about 1800 $s^{-1}$, about 1900 $s^{-1}$, about 2000 $s^{-1}$, about 2500 $s^{-1}$, about 800 $s^{-1}$, about 3000 $s^{-1}$, about 3500 $s^{-1}$, about 4000 $s^{-1}$, about 4500 $s^{-1}$, about 5000 $s^{-1}$, from about 500 $s^{-1}$ to about 5000 $s^{-1}$, from about 500 $s^{-1}$ to about 4000 $s^{-1}$, from about 500 $s^{-1}$ to about 3000 $s^{-1}$, from about 500 $s^{-1}$ to about 2000 $s^{-1}$, from about 500 $s^{-1}$ to about 1000 $s^{-1}$, from about 600 $s^{-1}$ to about 5000 $s^{-1}$, from about 600 $s^{-1}$ to about 4000

$s^{-1}$, from about 600 $s^{-1}$ to about 3000 $s^{-1}$, from about 600 $s^{-1}$ to about 2000 $s^{-1}$, from about 600 $s^{-1}$ to about 1000 $s^{-1}$, from about 700 $s^{-1}$ to about 5000 $s^{-1}$, from about 700 $s^{-1}$ to about 4000 $s^{-1}$, from about 700 $s^{-1}$ to about 3000 $s^{-1}$, from about 700 $s^{-1}$ to about 2000 $s^{-1}$, from about 700 $s^{-1}$ to about 1000 $s^{-1}$, from about 800 $s^{-1}$ to about 5000 $s^{-1}$, from about 800 $s^{-1}$ to about 4000 $s^{-1}$, from about 800 $s^{-1}$ to about 3000 $s^{-1}$, from about 800 $s^{-1}$ to about 2000 $s^{-1}$, or from about 800 $s^{-1}$ to about 1000 $s^{-1}$, etc., may be used. A fluid may be fed into the TFF system in addition to the RNA-containing sample. The fluid is typically a buffer. The choice and composition of the buffer may influence the efficiency of RNA purification and/or buffer exchange, levels of protein aggregation, RNA-protein separation and RNA stability. Typical buffer include those based on citric acid and Tris. The inventors have found that a Tris based buffer, for example containing 10 mM Tris, performs particularly well. Preferably, the buffer pH is between 6.5 and 9.0, between 7.0 and 8.5, between 7.5 and 8.5, between 7.8 and 8.2. More preferably, the sample buffer pH is 8.0.

For example, the pH of the buffer may be about 6.5, about 7.0, about 7.5, about 7.8, about 8.0, about 8.2, about 8.5, about 9.0, between about 6.5 to about 9.0, between about 6.5 to about 8.5, between about 6.5 to about 8.2, between about 6.5 to about 8.0, between about 7.0 to about 9.0, between about 7.0 to about 8.5, between about 7.0 to about 8.2, between about 7.0 to about 8.0, between about 7.5 to about 9.0, between about 7.5 to about 8.5, between about 7.5 to about 8.2, between about 7.5 to about 8.2, between about 7.8 to about 9.0, between about 7.8 to about 8.5, or between about 7.8 to about 8.2, etc. The buffer may further contain one or more salt(s), in addition to any buffering salts. Ideally, a salt type and concentration will be used such that RNA-protein interactions are weakened while maintaining the desired RNA in solution. For example, a total salt concentration of between 150 mM and 500 mM, or between 200 and 300 mM may be used. Preferably, the salt concentration is 250 mM. The salt may be sodium chloride.

For example, the buffer may contain one or more salt at a total salt concentration of between 0-500 mM, such as about 50 mM, about 75 mM, about 100 mM, about 150 mM, about 200 mM, about 250 mM, about 300 mM, about 350 mM, about 400 mM, about 450 mM, about 500 mM, from about 50 mM to about 500 mM, from about 50 mM to about 400 mM, from about 50 mM to about 300 mM, from about 50 mM to about 250 mM, from about 75 mM to about 500 mM, from about 75 mM to about 400 mM, from about 75 mM to about 300 mM, from about 75 mM to about 250 mM, from about 100 mM to about 500 mM, from about 100 mM to about 400 mM, from about 100 mM to about 300 mM, or from about 100 mM to about 250 mM, etc.

However, the inventors have found that excessive salt concentration in the buffer should ideally be avoided due to the risk of RNA precipitation during TFF or disadvantageous effects in any downstream methods. It is therefore preferred that no salt, other than buffering salts, is added to the buffer for TFF purification. Addition of EDTA to a buffer is known to advantageously inhibit any RNase activity. However, methods of the invention can purify RNA without the addition of EDTA, so the buffer may therefore be free from EDTA.

The volume ratio of the additional fluid (i.e. the fluid which is added beyond that of the sample) may influence the efficiency of the removal of small molecules during RNA purification and/or buffer exchange. However, larger volumes increase the operation time. Typically, the volume ratio of the additional fluid to that of the sample is between 5:1 and 10:1. The inventors have found that a ratio of about 8:1 is particularly advantageous to ensure efficient purification and/or buffer exchange without unduly increasing the operation time.

Hydroxyapatite Chromatography

The inventors have devised an industrially scalable process that is particularly useful for the purification of large RNA from IVT mixtures using hydroxyapatite chromatography, but can also be used for the purification of short (e.g. siRNA) and medium RNA (e.g. mRNA). Thus a method of the invention can comprise one or more steps of hydroxyapatite chromatography.

A particular advantage of this technique is that a step comprising enzymatic digestion of the template DNA can be omitted. This constitutes an improvement over prior art methods which rely on digestion of the template DNA. This method is particularly advantageous for efficiently removing template-derived DNA or fragments thereof, as well as proteins, from the desired RNA species.

Hydroxyapatite chromatography involves hydroxyapatite as stationary phase. Hydroxyapatite is a form of calcium phosphate having the chemical formula $[Ca_5(PO_4)_3(OH)]_2$. Hydroxyapatite chromatography of nucleic acids is believed to exploit the charge interaction between their negatively charged phosphate backbone and the positively charged calcium ions on the surface of the hydroxyapatite medium. Differential elution (e.g. to separate protein, DNA and undesired RNA species from desired RNA species) is accomplished by the application of an increasing phosphate gradient. Phosphate ions present in the buffer compete with the phosphate groups of the retained nucleic acid species for calcium on the hydroxyapatite medium, thus allowing separation by selective elution of molecules. In this mixed mode chromatography, the binding is a balance of attraction of the RNA phosphate backbone to the calcium ions of the hydroxyapatite medium and repulsion of the RNA phosphate backbone from the phosphate of the hydroxyapatite medium. Compared to ion exchange chromatography, the strength of the binding on a hydroxyapatite medium is dependent on charge density rather than total charge. This important difference allows for the separation of molecules upon their charge density (e.g. RNA vs DNA vs proteins) and the binding and elution of RNA regardless of its total charge, and therefore regardless of its length. Therefore this method can be used for the purification of RNA molecules of any length.

The fractionation of nucleic acids using hydroxyapatite was described in the 1960s (Bernardi et al. 1965). This approach has been exploited for applications including isolation and separation of viral RNA, dsDNA and ssDNA from environmental samples (Andrews-Pfannkoch et al. 2010), separation of DNA and RNA from tissue-extracted nucleic acids (Beland et al. 1979) and separation of DNA for hybridization studies (Kamalay et al. 1984). To the best knowledge of the inventors, there is no published evidence of the use of hydroxyapatite chromatography in a bioprocess for the purification of RNA obtained from IVT, which poses specific challenges to the skilled person due to the characteristics of the sample.

Hydroxyapatite chromatography parameters will be selected such that a desired RNA can be retained, and then selectively eluted, without significantly affecting RNA integrity and/or potency.

Hydroxyapatite chromatography may be performed using a batch format or a column format. A column format is preferred. The column comprises the stationary phase. Purification using a column format may include applying an RNA-containing sample to the column, discarding the flow-through, passing elution buffer through the column, and collecting the desired eluates or fractions thereof. The method may comprise additional steps such as wash steps before or during these steps. Suitable chromatography set-ups are known in the art, for example liquid chromatography systems such as the ÄKTA liquid chromatography systems from GE Healthcare.

A preferred hydroxyapatite stationary phase is ceramic hydroxyapatite. Ceramic hydroxyapatite is a spherical, porous form of crystalline hydroxyapatite and is typically obtained by sintering crystalline hydroxyapatite at high temperatures. Hydroxyapatite chromatography using ceramic hydroxyapatite as stationary phase is particularly advantageous for RNA purification a large-scale, as it is a particularly stable material that can withstand high flow rates and repeated use.

The nominal pore diameter of the hydroxyapatite particles is typically between 0.05-0.13 μm, for example 0.08-0.1 μm.

The nominal mean particle size is typically 20-80 μm, for example 40 μm.

An exemplary hydroxyapatite medium is CHT™ Ceramic Hydroxyapatite from Bio-Rad (Type II, 40 μm particle size).

The chromatography is typically performed at a linear flow rate of 250-350 cm/h, e.g. at 300 cm/h. Eluate fractions containing RNA may be identified by measuring UV absorption at 260 nm. The composition comprising the RNA of interest collected in the eluate is highly purified relative to the preparation before the hydroxyapatite chromatography step. Multiple eluted fractions containing the RNA of interest may be combined before further treatment.

Any suitable phosphate buffer may be used for elution. A particularly preferred phosphate buffer is one which minimises the levels of RNA precipitation compared to less preferred phosphate buffers when used at the same concentration and pH. The inventors have found that a potassium phosphate buffer is particularly suitable, and is preferred over a sodium phosphate buffer because it advantageously minimises the levels of RNA precipitation compared to a sodium phosphate buffer when used at the same concentration and pH. Generally, the inventors have found that using cations with increasing kosmotropicity are preferred.

The inventors have also found that hydroxyapatite chromatography parameters can be varied such that an improved separation of RNA and DNA is possible. This may be achieved by using an amount of a salt, in addition to the phosphate salt(s), in one or more of the elution buffer(s) such that the concentration of the salt in the final elution buffer remains constant throughout elution. Any suitable salt may be used, for example sodium chloride. Additionally or alternatively, an amount of a salt may be added to the sample before the sample is applied to the hydroxyapatite column. For example, potassium chloride or sodium chloride may be added to the sample to a final concentration of between 100-500 mM, e.g. 250 mM or 500 mM, and no salt is added to the phosphate elution buffer(s), provides a particularly advantageous method for purification of RNA with high yield while maintaining a high degree of purity.

For example, sodium chloride and/or potassium chloride may be added to the sample at a final concentration of between 0-500 mM, such as about 50 mM, about 75 mM, about 100 mM, about 150 mM, about 200 mM, about 250 mM, about 300 mM, about 350 mM, about 400 mM, about 450 mM, about 500 mM, from about 50 mM to about 500 mM, from about 50 mM to about 400 mM, from about 50 mM to about 300 mM, from about 50 mM to about 250 mM, from about 75 mM to about 500 mM, from about 75 mM to about 400 mM, from about 75 mM to about 300 mM, from about 75 mM to about 250 mM, from about 100 mM to about 500 mM, from about 100 mM to about 400 mM, from about 100 mM to about 300 mM, from about 100 mM to about 250 mM, etc.

The inventors have also found that, surprisingly, selective elution of RNA but not DNA or other impurities may be achieved by using an elution step wherein the phosphate concentration in the elution buffer is such that RNA is selectively eluted. The exact range of a suitable phosphate concentration may be determined empirically and depends on the presence of any additional non-phosphate salts in the elution buffer, such as sodium chloride. For example, where no additional salt is present, the inventors have found that using an elution step wherein the phosphate elution buffer has a conductivity of between about 1.8 S/m (18 mS/cm) and 3.8 S/m (38 mS/cm), or between 2.1 S/m (21 mS/cm) and 3 S/m (30 mS/cm), for example about 2.1 S/m (21 mS/cm) results in selective elution of RNA.

For example, the phosphate elution buffer may have a conductivity of about 1.8 S/m (18 mS/cm), about 1.9 S/m (19 mS/cm), about 2.0 S/m (20 mS/cm), about 2.1 S/m (21 mS/cm), about 2.2S/m (22 mS/cm), about 2.3 S/m (23 mS/cm), about 2.4 S/m (24 mS/cm), about 2.5 S/m (25 mS/cm), about 2.6 S/m (26 mS/cm), about 2.7 S/m (27 mS/cm), about 2.8 S/m (28 mS/cm), about 2.9 S/m (29 mS/cm), about 3.0 S/m (30 mS/cm), about 3.1 S/m (31 mS/cm), about 3.2 S/m (32 mS/cm), about 3.3 S/m (33 mS/cm), about 3.4 S/m (34 mS/cm), about 3.5 S/m (35 mS/cm), about 3.6 S/m (36 mS/cm), about 3.7 S/m (37 mS/cm), about 3.8 S/m (38 mS/cm), from about 1.8 S/m (18 mS/cm) to about 3.8 S/m (38 mS/cm), from about 1.8 S/m (18 mS/cm) to about 3.5 S/m (35 mS/cm), from about 1.8 S/m (18 mS/cm) to about 3.0 S/m (30 mS/cm), from about 1.8 S/m (18 mS/cm) to about 2.5 S/m (25 mS/cm), from about 1.8 S/m (18 mS/cm) to about 2.1 S/m (21 mS/cm), from about 2.0 S/m (20 mS/cm) to about 3.8 S/m (38 mS/cm), from about 2.0 S/m (20 mS/cm) to about 3.5 S/m (35 mS/cm), from about 2.0 S/m (20 mS/cm) to about 3.0 S/m (30 mS/cm), or from about 2.0 S/m (20 mS/cm) to about 2.1 S/m (21 mS/cm), etc.

This can be achieved for example by using an elution step using an elution buffer having a concentration of about 180 mM potassium phosphate. Suitable concentrations of other phosphate buffers (e.g. sodium phosphate) can also be used. Using a step-wise (non-continuous) elution gradient, comprising a step of selective RNA elution as described, is particularly advantageous for the purification of RNA.

The addition of a salt to the sample and/or elution buffer(s) and the use of a step-wise elution gradient, as mentioned above, can usefully be combined to obtain a particularly efficient separation of RNA from impurities. For example, the method may include using an amount of a salt, in addition to the phosphate salt(s), in one or more of the elution buffer(s) such that the concentration of the salt in the final elution buffer remains constant throughout elution, or adding an amount of a salt to the sample before applying the sample to the hydroxyapatite column (and optionally wherein no salt is added to the phosphate elution buffer(s)), and wherein the elution comprises an elution step wherein the phosphate concentration in the elution buffer is such that RNA is selectively eluted.

Preferably, hydroxyapatite chromatography is used according to the invention in combination with other RNA purification methods, for example hydroxyapatite chromatography may be preceded by a method that efficiently removes free nucleotides, because the inventors have surprisingly found that these can block or saturate the column. The inventors have found that such a combination of methods results in particularly efficient purification of large RNA from an in vitro transcription sample. For example, core bead flow-through chromatography or tangential flow chromatography may be used as a purification step preceding hydroxyapatite chromatography.

Core Bead Flow-Through Chromatography

According to the invention, RNA may be purified using core bead flow-through chromatography. Thus a method of the invention can comprise one or more steps of core bead flow-through chromatography. The inventors have found that this technique enables a fast, industrial-scale purification process for obtaining pure RNA with high yield, and is particularly advantageous for removing protein contaminants from a desired RNA species e.g. in an IVT reaction sample. The inventors have shown that very large RNA species comprising more than 3 megadaltons may be purified using this method. To the best knowledge of the inventors, there are no prior art methods that enable the purification of such large RNA species, in particular after IVT, using core bead chromatography or any other methods. However, this method is not limited to the purification of large RNA molecules, and RNA molecules of any size (e.g. medium RNAs) can be purified with this method as long as a suitable bead pore size is selected, as described below.

Core bead flow-through chromatography may be performed using a batch format or a column format. A column format is preferred. The column comprises the stationary phase. The column format may include applying a RNA-containing sample to the column, collecting the flow-through, and optionally passing elution buffer through the column, and collecting the desired eluates or fractions thereof. The method may comprise additional steps such as wash steps e.g. after applying the sample to the column, a "chase" buffer is usually added to the column. Suitable chromatography setups are known in the art, for example liquid chromatography systems such as the ÄKTA liquid chromatography systems from GE Healthcare.

After applying the RNA-containing sample to the column, its contents can travel through the column by gravitational force alone or external pressure may be applied to increase the rate of their passage. Following application of the RNA-containing sample to the column, a buffer may also be applied to the column, typically called a "chase buffer" in the art, and passed through the column using gravitational force alone or by applying external pressure in order to increase the rate at which the sample components pass through the column. The flow rate can be stated as volumetric flow rate (volume of mobile phase, e.g. sample and/or chase buffer, passing through the column per unit time) or linear flow rate (distance of mobile phase front travelled per unit time). Methods to calculate the flow rate and convert from linear to volumetric flow rate are known in the art.

According to the invention, the chromatography medium is comprised of beads that are comprised of a porous material (matrix), usually formed from a polymer. The matrix comprises at least two layers, for example an inner layer (core) surrounded by an outer layer (shell), but the matrix may also comprise one or more additional (intermediate) layers between the inner layer and the outer layer.

Each matrix layer may be functionalised with at least one ligand, or it may not be functionalised. Typically, the layers can be distinguished from each other by the presence or absence of at least one ligand.

For example, the core may be functionalised with N different ligands, whereas the shell is functionalised with no more than N−1 of these ligands. N may be any positive integer, for example 1. For example, the core may be functionalised with a ligand whereas the shell is functionalised with one or more different ligands, or may not be functionalised with any ligand. In a preferred embodiment, the core is functionalised with a ligand, whereas the shell is not functionalised with any ligands.

Preferably, at least one ligand is a ligand that has multiple functionalities, for example the ligand is both hydrophobic and positively charged. For example, the ligand may be a mono-(C1-C8)alkyl-amine, for example the ligand may be octylamine ($CH_3(CH_2)_7NH_2$).

Thus in a preferred embodiment of the invention, the core is functionalised with a ligand, wherein the ligand has multiple functionalities, for example the ligand is both hydrophobic and positively charged, for example the ligand may be a mono-(C1-C8)alkyl-amine, for example the ligand may be octylamine, and the shell is not functionalised with any ligands.

The matrix has a defined pore size and thereby prevents a proportion of molecules from entering the core based on the size of the molecules, which are collected in the column flow-through (flow-through mode). Molecules that are able to pass through the matrix enter the core, where they may be retained, typically by binding to a ligand. Retained molecules may be eluted from the beads using a suitable eluent (bind-elute mode). Typically, the eluent is a solution comprising sodium hydroxide (NaOH) and a solvent.

Core bead flow-through chromatography parameters will be selected such that a desired RNA can be selectively recovered from one or more of the flow-through fraction(s), without significantly affecting RNA integrity and/or potency.

Preferably, the matrix is a porous matrix, for example agarose, preferably a highly cross-linked agarose.

The matrix pore size is usually stated in kDa and refers to the average molecular mass of the smallest particle the matrix is likely to reject (also referred to as MWCO). Alternatively, the matrix pore size can be stated in µm and refers to the diameter of the smallest particle the matrix is likely to reject, as described above for TFF. The pore size is selected so that the cut-off is below RNA size but above protein size. Using this method, RNA species may be purified that ARE larger than the molecular cut-off of the beads. More preferably, the desired RNA species is the largest molecule in the sample to be purified. Therefore, according to this invention RNA is recovered from one or more of the flow-through fraction(s).

The inventors have found that for the purification of large RNAs a MWCO/pore size of at least 250 kDa is useful e.g. at least 300 kDa, 400 kDa, 500 kDa, 600 kDa, or at least 700 kDa etc. A molecular weight cut-off of at least about 700 kDa is particularly preferred. Generally, the MWCO is selected such that the ratio of the molecular weight of the RNA molecule of interest to the MWCO is at least 1.5:1 (e.g. at least 2:1, at least 3:1, at least 4:1, at least 5:1 or at least 6:1) and/or that the ratio of the molecular weight of the largest non-RNA impurity to the MWCO is at least 1:1.5 (e.g. at least 1:2, at least 1:3, at least 1:4, at least 1:5 or at least 1:6).

The average diameter (particle size) of the beads will be selected so to enable efficient RNA purification with minimal operation time without significantly affecting RNA integrity and/or potency due to excessive pressures required for performance. Larger particles and larger pores typically allow the use of lower pressures, but the separation efficiency may be reduced. The inventors have found that a particle size of about 50-100 µm is preferable, wherein a particle size of about 60-90 µm is more preferably, and wherein a particle size of about 70-80 µm is even more preferable. A particle size of about 85 µm is most preferred.

An exemplary core bead flow-through chromatography medium is Capto™ Core 700 beads from GE Healthcare.

RNA is selectively recovered from the column in the flow-through. Proteins and short nucleic acids are retained in the beads. Flow-through fractions containing RNA may be identified by measuring UV absorption at 260 nm. The composition comprising the RNA of interest collected in the flow-through is highly purified relative to the preparation before the core bead chromatography step. Multiple eluted fractions containing the RNA of interest may be combined before further treatment.

An amount of a salt may be added to the RNA-containing sample before the sample is passed through the column. The inventors have found that this is particularly advantageous for the removal of protein impurities. Any suitable salt may at a suitable concentration be used, for example at between about 150 mM and 500 mM.

For example, a salt may be added to the RNA-containing sample at a final concentration of between 0-500 mM, such as about 50 mM, about 75 mM, about 100 mM, about 125 mM, about 150 mM, about 200 mM, about 250 mM, about 300 mM, about 350 mM, about 400 mM, about 450 mM, about 500 mM, about 600 mM, about 700 mM, about 750 mM, from about 50 mM to about 600 mM, from about 50 mM to about 550 mM, from about 50 mM to about 500 mM, from about 50 mM to about 400 mM, from about 100 mM to about 600 mM, from about 100 mM to about 550 mM, from about 100 mM to about 500 mM, from about 100 mM to about 400 mM, from about 150 mM to about 600 mM, from about 150 mM to about 550 mM, from about 150 mM to about 500 mM, from about 150 mM to about 400 mM, etc.

The inventors have found that a salt concentration of between about 125 mM and 250 mM is particularly advantageous, resulting in RNA purification with a high RNA yield and efficient protein removal. Alternatively, where a high RNA yield is required more than removal of protein impurities, for example where a sample that is substantially free from protein is used, a salt concentration of not more than 250 mM, or preferably not more than 125 mM can be used. Where a high RNA yield and/or high efficiency of nucleotide removal is required more than removal of protein impurities, for example where a sample that is substantially free from protein but contains large amounts of free nucleotides is used, a salt concentration of not more than 250 mM, preferably not more than 125 mM, and most preferably no salt is added.

A suitable salt is typically a salt which minimises the levels of RNA precipitation compared to less preferred salts when used at the same concentration and pH. The inventors have found that typically potassium phosphate and/or potassium chloride are particularly suitable, and preferred over sodium phosphate and sodium chloride, because potassium salts advantageously minimises the levels of RNA precipitation compared to sodium salts when used at the same concentration and pH. Generally, the inventors have found that using cations with increasing kosmotropicity is preferred.

The RNA-containing sample may be diluted before the sample is passed through the column. For example, the sample may be diluted with a diluent volume that corresponds to about 5-fold, about 4-fold, about 3-fold, about 2-fold, or about 1-fold of sample volume. A 1-fold dilution means that a volume of a diluent that is equal to the volume of the sample is added to the sample. Any suitable diluent may be used and will typically be a buffer. A suitable diluent is one that does not interfere with any subsequent purification or buffer exchange steps. For example, the diluent may be a buffer that is the same as the buffer of the RNA-containing sample (e.g. 50 mM Tris, pH 8.0).

The flow rate may be varied to achieve improved RNA recovery and/or protein removal. A linear flow rate of between 200 and 500 cm/h is advantageous where a high RNA recovery is desired. A flow rate of between 50 and 300 cm/h is advantageous where a high level of protein removal is desired. Typically, a flow rate of between 250 and 300 cm/h, preferably of about 275 cm/h is used for optimised recovery and protein removal.

The addition of a salt, dilution of the sample, and variation of the flow rate, as described above, can usefully be combined. For example, the RNA-containing sample may be diluted and an amount of a salt may be added to the sample before the sample is passed through the column. A particularly advantageous method for the purification of large RNA with high purity, yield and short operation times is one where sample is diluted 4-fold before applying the sample to the column, the chromatography is performed at a linear flow rate of 275 cm/h and salt is added to the sample and/or chase buffer at 250 mM (e.g. KCl or NaCl).

Where core bead chromatography is used according to the invention, it is particularly useful for removing protein contaminants from an RNA of interest. Particularly good results are achieved where the RNA-containing sample that is applied to the chromatography column in a single purification run contains no more than 5-15 mg total protein per ml of stationary phase (i.e. core beads), e.g. no more than 10 mg/ml or no more than 13 mg/ml. These values are particularly relevant where the total protein is composed of proteins that are typically components of an in vitro transcription reaction, such as T7 polymerase, capping enzyme, RNase inhibitor and pyrophosphatase.

Where large-scale purification is performed, chromatography columns may be connected to each other in series for increased capacity.

The inventors have also found that even higher levels of purity (e.g. by more efficiently removing free nucleotides remaining from NT) can be achieved where a step of core bead flow-through chromatography is followed by a step of TFF. The TFF step can be used to simultaneously perform RNA purification, in particular nucleotide removal, and buffer exchange by using a formulation buffer during the purification/buffer exchange process. The formulation buffer is different to the purification buffer used in any preceding steps.

Combination of Methods

Any of the disclosed methods can be used in isolation or combined in a process comprising at least one step of RNA purification, and optionally a further step of buffer exchange. For example, TFF, core bead flow-through chromatography, or hydroxyapatite chromatography is used for RNA purification, optionally followed by a further step of TFF for buffer exchange and/or RNA purification.

In another example, TFF is used in combination with hydroxyapatite chromatography for RNA purification, optionally followed by a further step of TFF for buffer exchange and/or RNA purification.

In another example, core bead flow-through chromatography is used in combination with hydroxyapatite chromatography for RNA purification, optionally followed by a step of TFF for buffer exchange and/or RNA purification.

In another example, TFF is used in combination with core bead flow-through chromatography for RNA purification, optionally followed by a further step of TFF for buffer exchange and/or RNA purification.

In another example, where core bead flow-through chromatography is used, it is followed by tangential flow filtration. Such a method may also include hydroxyapatite chromatography which follows core bead flow-through chromatography and precedes tangential flow filtration.

In another example, where hydroxyapatite chromatography is used, it is preceded by tangential flow filtration or core bead flow-through chromatography. Such a method may also include tangential flow filtration which follows hydroxyapatite chromatography.

Where a combination of methods comprises two steps of the same method, e.g. one step of tangential flow filtration and a further step of tangential flow filtration, two different buffers are typically used in the first step and in the second step. Typically, the first buffer is different from the second buffer in at least one component and/or characteristic. For example, the salt concentration, type of salt, tonicity, pH or amount of contaminants may be different. Usually, the buffers will be based on different buffering systems, for example the first buffer may be a Tris or phosphate-based buffer, whereas the second buffer is a citrate-based buffer.

The inventors have shown that a combination of methods as recited above leads to even greater advantages in terms of purity (e.g. removal of ribonucleoside triphosphates, proteins, DNA and fragments thereof) and yield of the final RNA product, ease of operation, time efficiency and scalability of the overall process.

Apparatus Characteristics

One advantage of the invention is that it uses components which are disposable. Thus a method of the invention can include a step in which some or all of the apparatus in which the method is performed are discarded after the method is performed. For instance, any TFF columns, hydroxyapatite supports, and/or core bead flow-through columns can be discarded, as can any tubing and connectors which were used to connect them. These components may be discarded as biohazardous waste.

Thus methods of the invention can use disposable apparatus components. Furthermore, methods of the invention will, in general, use apparatus components that can readily be decontaminated from RNase. This requirement can be reflected in the materials, shape, configuration and dimensions of the components.

Quick Methods

As mentioned above, the invention provides a method for purifying RNA from a sample, wherein the RNA is purified to at least 99% purity in less than 12 hours.

Similarly, the invention provides a method for purifying RNA from a sample which contains RNA, DNA, pyrophosphates, and free nucleotides (as un-reacted RNA precursors and/or as degradation products from RNA or DNA), wherein the method provides final material in less than 12 hours which is free from DNA, pyrophosphates, and free nucleotides.

The RNA-containing sample can be the product of an IVT reaction, and so will contain the typical IVT contaminants discussed above.

The RNA can be prepared to a high purity e.g. ≥99.5%, ≥99.9%, or even ≥99.95%. Thus at least 99% or more of the components in the purified material (other than water and buffer salts) are a RNA of interest.

The method can be completed, to provide the purified RNA, in less than 12 hours e.g. <8 hours, <6 hours, <4 hours, or <2 hours.

The method can use any of the steps (and combinations thereof) disclosed elsewhere herein. The method is ideally performed using aqueous conditions throughout.

Pharmaceutical Compositions

RNA purified according to this invention is useful as a component in pharmaceutical compositions, for example for use as a vaccine in immunising subjects against various diseases. These compositions will typically include RNA and a pharmaceutically acceptable carrier. A thorough discussion of pharmaceutically acceptable carriers is available in Gennaro et al. A pharmaceutical composition of the invention can also include one or more additional components such as small molecule immunopotentiators (e.g. TLR agonists). A pharmaceutical composition of the invention can also include a delivery system for the RNA e.g. a liposome, an oil-in-water emulsion, or a microparticle.

A pharmaceutical composition of the invention is preferably substantially free from contaminants resulting from RNA manufacture and purification. Where NT is used, such contaminants may include proteins, e.g. enzymes such as polymerase, in particular T7 polymerase, and capping enzymes, free nucleotides, and template DNA &/or fragments thereof.

Pharmaceutical compositions of the invention may include the RNA in plain water (e.g. w.f.i.) or in a final formulation buffer e.g. a phosphate buffer, a Tris buffer, a borate buffer, a succinate buffer, a histidine buffer, or a citrate buffer. Buffer salts will typically be included in the 5-20 mM range.

Compositions of the invention may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity.

Compositions of the invention may include sodium salts (e.g. sodium chloride) to give tonicity. A concentration of 10±2 mg/ml NaCl is typical e.g. about 9 mg/ml.

Pharmaceutical compositions of the invention may have a pH between 5.0 and 9.5 e.g. between 6.0 and 8.0.

Pharmaceutical compositions of the invention may have an osmolality of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines can be prepared. Pharmaceutical compositions of the invention are preferably sterile.

Pharmaceutical compositions of the invention are preferably non-pyrogenic e.g. containing <1 EU (endotoxin unit, a standard measure) per dose, and preferably <0.1 EU per dose.

Pharmaceutical compositions of the invention are preferably gluten free.

Pharmaceutical compositions of the invention may be prepared in unit dose form. In some embodiments a unit dose may have a volume of between 0.1-1.0 ml e.g. about 0.5 ml.

The compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Where a composition includes a delivery system, this will usually be a liposome (e.g. see WO2012/006376, WO2012/030901, WO2012/031043, WO2012/031046, and WO2013/006825), an oil-in-water emulsion (e.g. see WO2012/006380, WO2013/006834, and WO2013/006837), or a microparticle (e.g. see WO2012/006359). A process of the invention may include a further step of combining a purified RNA molecule with a delivery system. Similarly, the invention provides a method for preparing a pharmaceutical composition, comprising steps of: purifying a RNA using a method of the invention; and combining the purified RNA with a delivery system e.g. with a liposome or with an oil-in-water emulsion.

Compositions comprise an immunologically effective amount of RNA, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The RNA content of compositions of the invention will generally be expressed in terms of the amount of RNA per dose. A preferred dose has ≤100 µs RNA (e.g. from 10-100 µg, such as about 10 µg, 25 µg, 50 µg, 75 µg or 100 µg), but expression can be seen at much lower levels e.g. ≤1 µg/dose, ≤100 ng/dose, ≤10 ng/dose, ≤1 ng/dose, etc.

The invention also provides a delivery device (e.g. syringe, nebuliser, sprayer, inhaler, dermal patch, etc.) containing a pharmaceutical composition of the invention. This device can be used to administer the composition to a vertebrate subject.

Methods of Treatment and Medical Uses

Pharmaceutical compositions of the invention can be used in vivo for eliciting an immune response against an immunogen of interest.

The invention thus provides a method for raising an immune response in a vertebrate comprising the step of administering an effective amount of a pharmaceutical composition of the invention. The immune response is preferably protective and preferably involves antibodies and/or cell-mediated immunity. The method may raise a booster response.

The invention also provides a pharmaceutical composition of the invention for use in a method for raising an immune response in a vertebrate.

The invention also provides the use of a pharmaceutical composition of the invention in the manufacture of a medicament for raising an immune response in a vertebrate.

By raising an immune response in the vertebrate by these uses and methods, the vertebrate can be protected against various diseases and/or infections e.g. against bacterial and/or viral diseases as discussed above. The compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to elicit systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

General

The practice of the present invention will employ, unless otherwise indicated, conventional methods of chemistry, biochemistry, molecular biology, immunology and pharmacology, within the skill of the art. Such techniques are explained fully in the literature.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to charge, to cations, to anions, to zwitterions, etc., are taken at pH 7.

The term "yield" in the context of this invention stands for the fraction of RNA contained in sample after purification compared to before purification. Typically, yield is expressed as % yield, calculated according to the formula: [(amount RNA post-purification/amount RNA pre-purification)×100]. RNA amounts in a sample can be measured using methods known in the art, for example using an RNA-specific fluorescent dye such as RiboGreen®.

The term "purification" or "purify" means that a desired RNA in a sample is separated from undesired components. "RNA purification" thus refers to methods for purifying a RNA of interest from a composition comprising the RNA of interest and impurities. Thus, after purification the RNA is present in a purer form than before purification. This means that undesired components are present at lower amounts relative to the amount of desired RNA than before purification. Undesired constituents of RNA-containing samples which may need to be separated from the desired RNA may include DNA, deoxynucleoside monophosphates, ribonucleoside triphosphates, undesired RNA species (e.g. RNA that is longer/shorter than a desired RNA size or outside a desired RNA size range, or double-stranded RNA vs single-stranded RNA), deoxy-oligonucleotides, proteins (in particular enzymes such as RNA polymerases e.g. T7 polymerase, mRNA capping enzyme, pyrophosphatase, DNase, RNase inhibitors), etc.

The words "potency" or "functionality" describe the intended biological function of the RNA molecule and the level to which that function is retained after purification compared to before purification of the RNA. For example, if the RNA potency remains unchanged after purification, then the extent of a particular biological function of the RNA has not changed, for example as measured by the in vivo expression level of any encoded protein relative to a certain amount of input RNA.

The word "stability" refers to the extent to which an RNA molecule retains its structural integrity and resists degradation during physical or chemical manipulations. For example, if RNA stability remains unchanged after purification, then the level of structural integrity has not changed, for example measured by analysing the average RNA size or the RNA size distribution.

The terms "preparative", "large scale", "commercial scale" and "industrial scale" in relation to a RNA purification method mean that large quantities of RNA can be purified to a purity of at least 90%. Such large quantities are for example at least 0.5 mg, 1 mg, 2.5 mg, 5 mg, 10 mg, 25 mg, 50 mg, 100 mg, 250 mg, 500 mg, or even at least 1000 mg using the method of the invention.

The term "stationary phase" refers to the non-mobile phase contained in a chromatographic bed.

The term "particle size" refers to the average diameter of a stationary phase particle.

The term "pore size" refers to the average size of the smallest particle that a stationary phase will reject or that a membrane will retain on the sample side. The size is typically expressed in particle diameter or molecular mass.

The term "elution gradient" means that the composition of the eluent is varied throughout the elution process in a continuous or step-wise manner. In contrast, "isocratic elution" proceeds using a fixed eluent composition throughout the elution process.

A "step" is different from another step of RNA purification or buffer exchange where the steps use different methods (e.g. tangential flow filtration vs. hydroxyapatite chromatography) or where the steps use the same method but are performed under different conditions (e.g. using a different buffer, a different membrane, or a different stationary phase).

When a second step is performed "after" or "following" another first step, the second step may be performed immediately after the previous first step in the method, i.e. no other step is performed between the first step and the second step, other than steps such as dilution or storage which may take place in between the two steps. Alternatively, other step(s) may be performed between the first and second steps.

When a first step is performed "before" or "preceding" another second step, the first step may be performed immediately before the subsequent step in the method, i.e. no other steps are performed between the first step and the second step, other than steps such as such as dilution or storage which may take place in between the two steps. Alternatively, other step(s) may be performed between the first and second steps.

BRIEF DESCRIPTION OF DRAWINGS

FIGS. 2A-2B show the result of RNA purification using hydroxyapatite chromatography. FIG. 2A illustrates Hofmeister series of ions in order of their ability to salt out proteins. FIG. 2B shows the dynamic light scattering analysis of RNA aggregate particle size in various elution buffers—x-axis: salt concentration in mM; y-axis: particle radius in nm.

FIG. 6A shows the result of quantification of RNA or RNA plus nucleotides. FIG. 6B and FIG. 6D show the result of tangential flow filtration vs. core bead flow-through chromatography—in vitro transcription reaction sample—nucleotide removal. FIG. 6C shows the result of tangential flow filtration vs. core bead flow-through chromatography vs. core bead flow-through chromatography and hydroxyapatite chromatography vs. tangential flow filtration and hydroxyapatite chromatography—in vitro transcription reaction sample—protein removal.

FIG. 7A shows recovery of RNA measured by direct quantification by RiboGreen® assay (sample dilution 10'000 fold). FIG. 7B shows the purity of RNA sample by quantitative ELISA (T7 polymerase, samples in italics are below LOQ). The graph shows detectable T7, below LOQ for most samples by ELISA. FIG. 7C shows the purity of RNA sample by quantitative ELISA (capping enzyme, samples in italics are below LOQ, "0" equals below LOD). The graph shows capping enzyme below LOD in sample P3, post CC250 and P2 and P4, post HTP. FIG. 7D shows the purity of RNA sample by SDS page—silver staining (4 µg RNA loaded per lane). FIG. 7E shows nucleotide removal, expressed as ratio of quantification by OD/quantification by RiboGreen® (Y-axis refers to OD/RiboGreen®). FIG. 7F shows plasmid DNA carryover, using qPCR assay on plasmid. DNA before purification: 1.0 ng/dose. Following purification: 0.6/0.7 ng/dose. Lowest concentration was found after HTP chromatography. Same TFF cartridge was used in all 4 processes/steps: possible carryover. No background (buffer) control was used in this experiment. FIG. 7G shows the level of *E. coli* protein contamination, using host (*E. coli*) protein oat polyclonal antibodies (HRP labelled) to *E. coli*. In this assay L.O.D. (limit of detection) is 1 ng/band, 4 ug RNA was loaded in each lane. The figure shows that host contaminant below 1 ng/protein.

Figure 1:
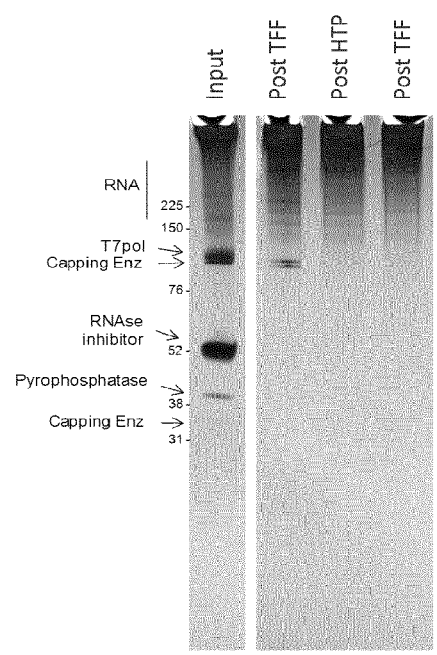
FIG. 1 shows the result of RNA purification using tangential flow filtration and hydroxyapatite chromatography: in vitro transcription reaction sample—protein removal—in vitro transcription reaction sample before purification (lane 1), after tangential flow filtration (lane 2), after hydroxyapatite chromatography (lane 3), after tangential flow filtration (lane 4).

Factors chosen for the study and range:

| | Range | | Outputs: |
|---|---|---|---|
| | −1 | +1 | Recovery<br>T7 removal<br>Capping enz Removal |
| Flow (cm/h) | 50 | 500 | Nucleotides removal |
| Salt | 0 | 500 | Precolumn pressure |
| Conc | 0.25 | 1 | Time |

MODES FOR CARRYING OUT THE INVENTION

Example 1: Method for Quantifying RNA Yield and Nucleotide Removal

RNA was quantified in samples using an RNA-specific fluorescent dye (RiboGreen®). RNA levels before and after purification were compared to calculate % RNA yield. RiboGreen® does not detect free nucleotides.

Free nucleotides are found in the unpurified in vitro transcription (NT) reaction and include un-reacted precursors for RNA (ribonucleoside triphosphate) and degradation products from DNAse digestion (deoxynucleosides monophosphate). A method was developed to measure nucleotides in the presence of RNA. Pure RNA was measured with RiboGreen® (FIG. 6A, $1^{st}$ bar) and by optical density (OD) at 260 nm, using 40 as a standard approximated extinction coefficient for RNA ($2^{nd}$ bar). A mix of nucleotides was added to the pure RNA sample in a ten-fold excess to RNA by mass. The resulting samples were measured again with RiboGreen® (3' d bar) and by OD ($4^{th}$ bar).

The results show that the measurement by RiboGreen® is unaffected by the presence of nucleotides in the sample, while the detected OD values reflect the total concentration of RNA and nucleotides in the sample. The presence of nucleotides, as an indicator for nucleotide removal after an RNA purification step, was calculated as the ratio of the OD measurement and the RiboGreen® assay measurement. A ratio of approximately 1 indicates pure RNA, i.e. complete nucleotide complete. Ratios above 1 indicate the presence of nucleotides in the sample.

Example 2: RNA Purification and Buffer Exchange Using Tangential Flow Filtration A 10-kb RNA replicon was produced through in vitro transcription and capping with completely chemical-defined enzymes, template, substance and buffers. A KrosFlo Research IIi Tangential Flow Filtration System was used (Spectrum Laboratories) for both RNA purification and buffer exchange in one single closed system. Various parameters were tested for optimal results as indicated below: membrane chemistry, membrane pore size, membrane area, transmembrane pressure, shear rate (retentate velocity), buffer volume, buffer capacity, buffer pH, sample salt concentration, and the presence of EDTA in the buffer.

| TFF cartridge | | | |
|---|---|---|---|
| Parameters considered for optimization | Theoretical impact on RNA quality | Conditions screened | Condition selected |
| Membrane chemistry | Interaction of membrane with RNA and protein RNA recovery and protein removal | mPES, PS (Spectrum and Watersep) | mPES from Spectrum |
| Membrane pore size | Retain large MW particle and remove small MW molecules RNA recovery and protein removal | 500 kD, 750 kD MWCO 0.05 and 0.1 µm | 500 kD MWCO |
| Membrane area | Buffer exchange efficiency Operation time | 25, 52, 115 $cm^2$ | 115 $cm^2$ |

| TFF system variables | | | |
|---|---|---|---|
| Parameters considered for optimization | Theoretical impact on RNA quality | Conditions screened | Condition selected |
| TMP (transmembrane pressure) | RNA/protein separation Gel layer formation | 1-5 Psi | 2 Psi |
| Shear rate (retentate velocity) | RNA integrity Gel layer formation | 1000-5000 S$^{-1}$ | ~800 S$^{-1}$ |
| Dialysis buffer volume | Small molecule removal Buffer exchange efficiency operation time | 5x-10x sample volume | 8x sample volume |

| Purification buffer | | | |
|---|---|---|---|
| Parameters considered for optimization | Theoretical impact on RNA quality | Conditions screened | Condition selected |
| Buffer capacity | Buffer exchange efficiency (buffer change from RNA synthesis and to formulation) | 2, 10 mM Citrate and 10, 50 mM Tris | 10 mM Tris |
| Buffer pH | Interaction of RNA with protein Protein aggregation | pH 6.5, 7.0, 7.5, 8.0, 8.5 and 9.0 | pH 8.0 |
| Salt concentration | Interaction of RNA with protein | 150, 250 and 500 mM NaCl | 250 mM NaCl |
| EDTA | Interaction of RNA with RNA binding protein RNA stability | 0, 1, 10, and 20 mM | 0 mM Stability |

Four consistency runs were performed using the optimised conditions and demonstrated that the tangential flow filtration method purifies RNA with high recovery (>95%), purity as measured by protein removal (>90% of T7 RNA polymerase removed, as quantified by ELISA; 5 ng T7 polymerase per 75 ug RNA post purification; >95% vaccinia capping enzyme removed, as quantified by ELISA) and as measured by nucleotide removal (>99.9% of free nucleotides removed, as quantified using the assay of Example 1), potency (no change in potency after purification) and stability (RNA is stable after purification). The operation as a single closed system prevents contamination with exogenous agents such as RNase. The method is quick (approx. 70 mins total) and easy to operate.

Figure 5:
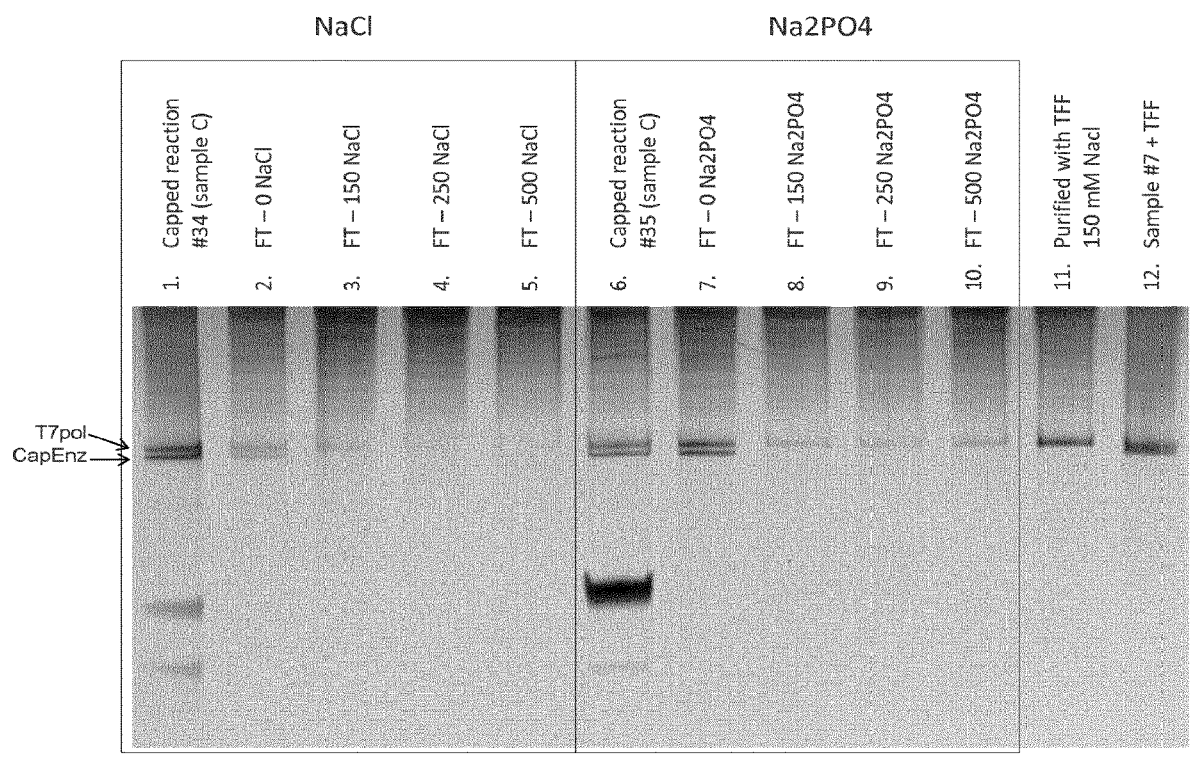
FIG. 5 shows the result of RNA purification using core bead flow-through chromatography: in vitro transcription reaction sample—effect of salt in sample and chase buffer on protein removal.
Figure 7A:
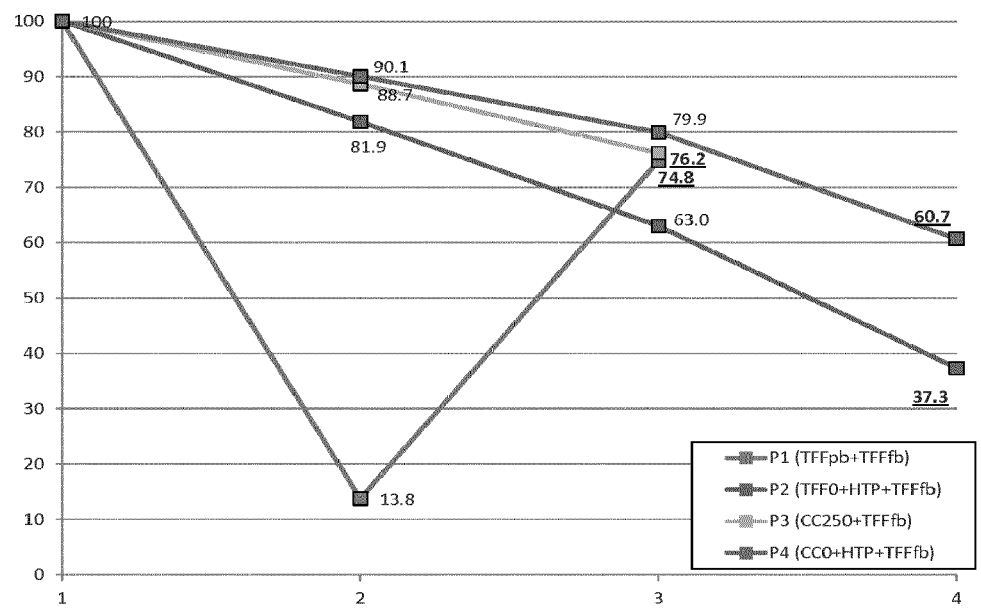
FIGS. 7A-7G show the result of RNA purification using combination of methods described herein: in vitro transcription reaction sample—effect on RNA recovery, protein removal, nucleotide removal and DNA removal.
Figure 7B:
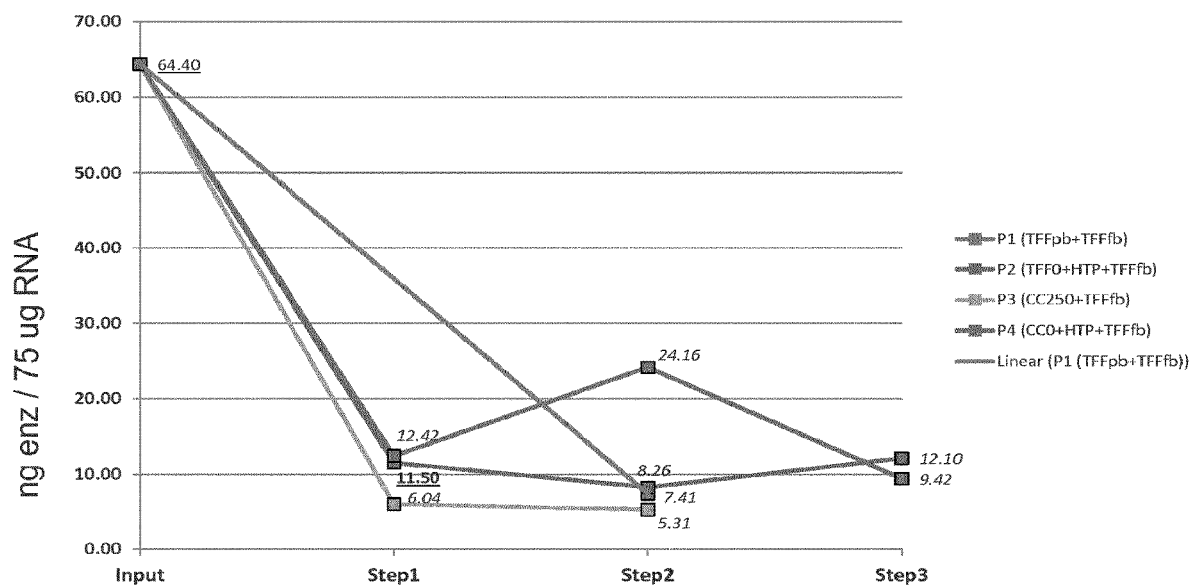
Figure 7C:
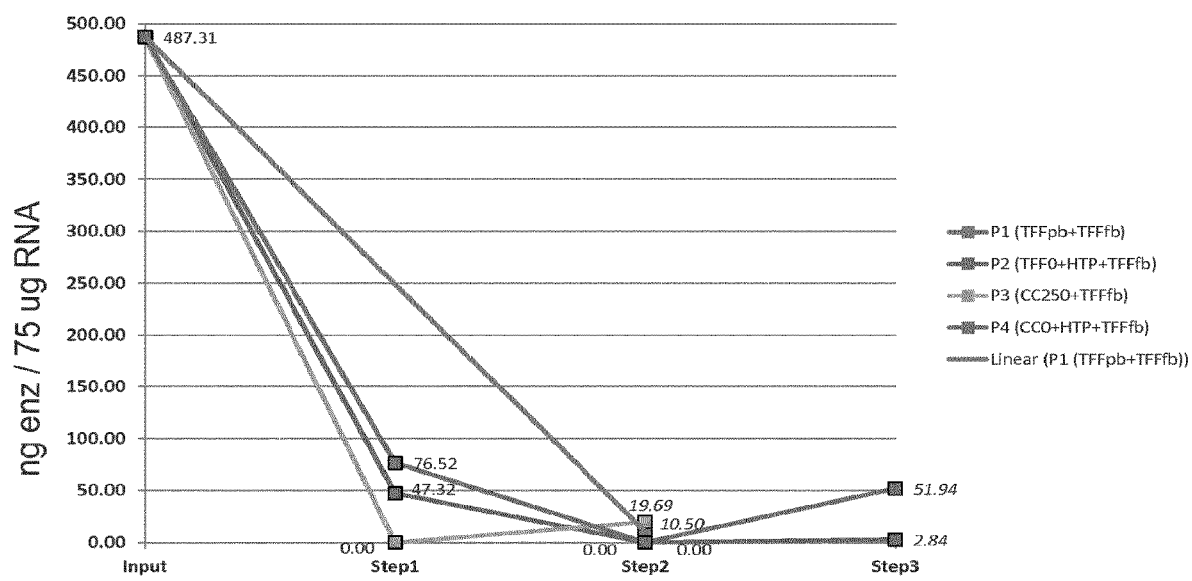
Figure 7D:
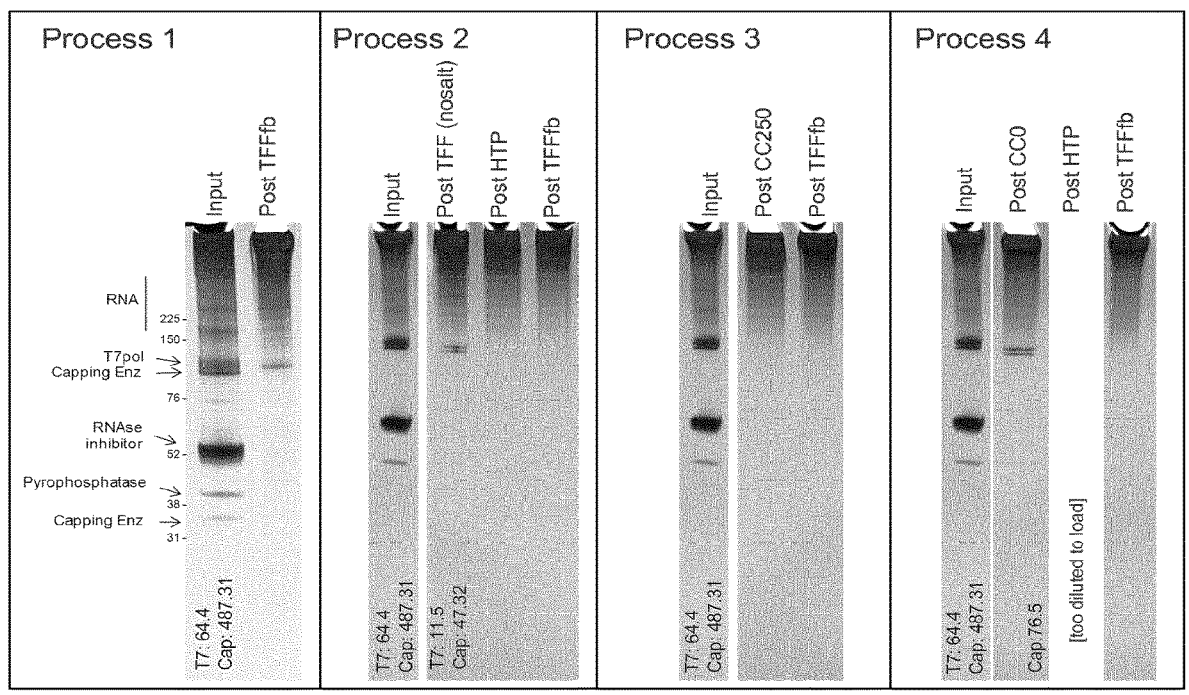
Figure 7E:
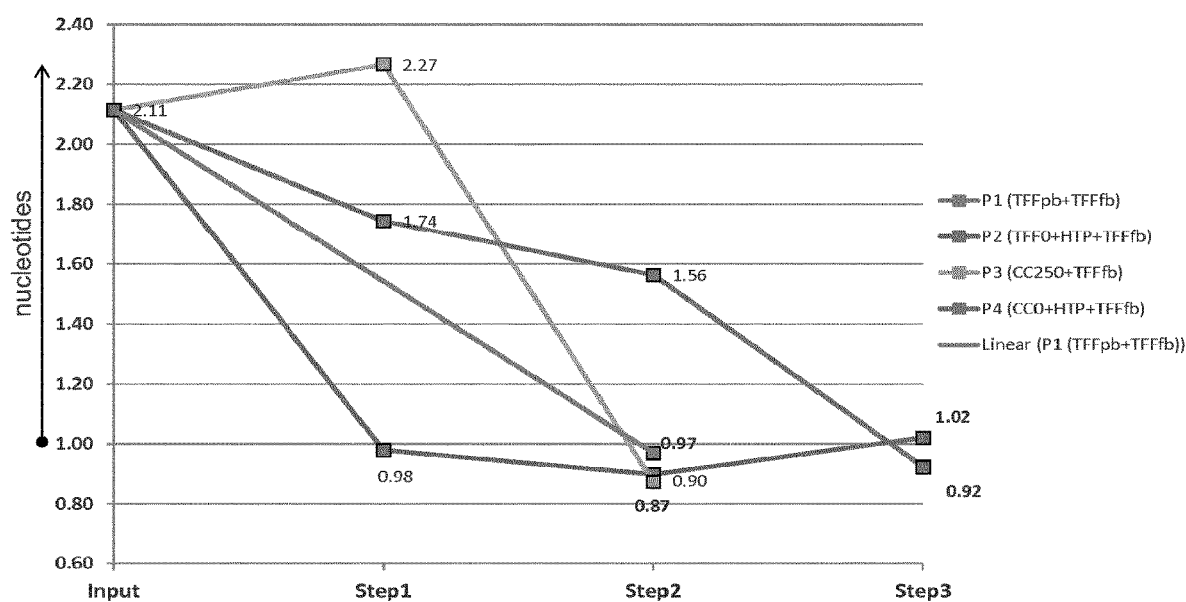
Figure 7F:
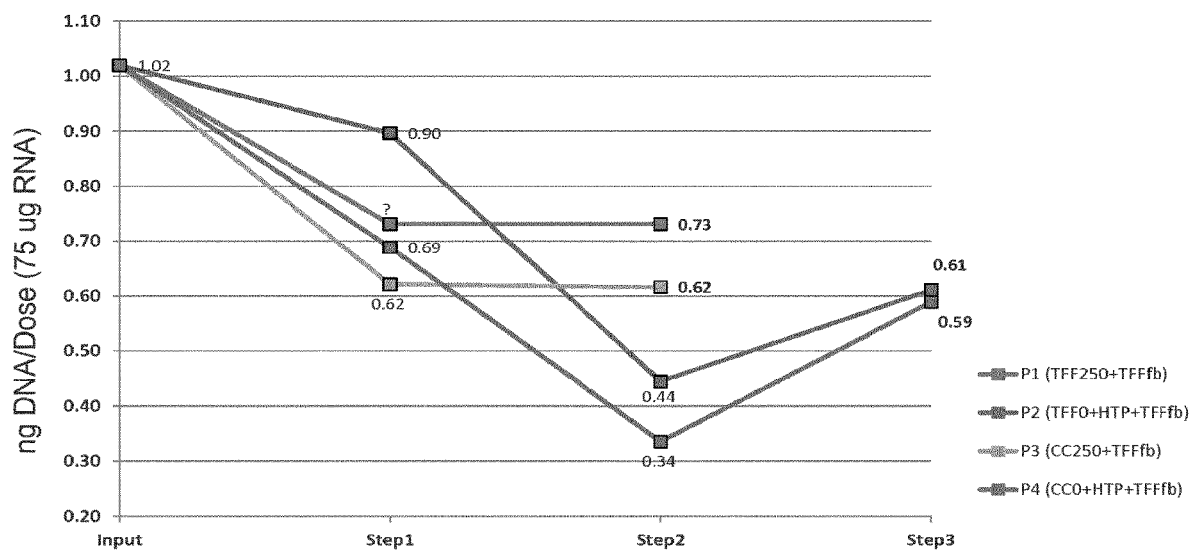
Figure 7G:
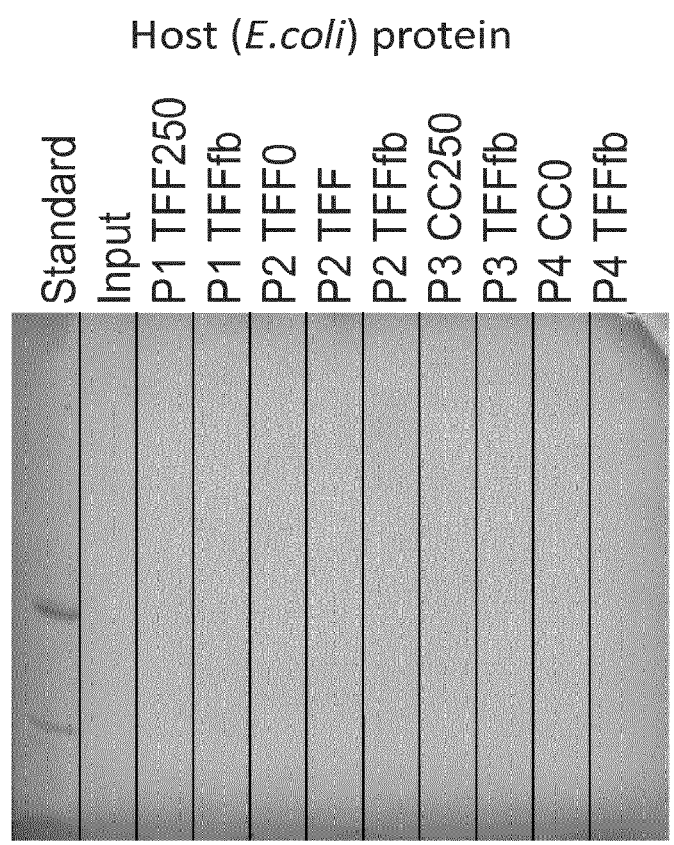

As shown in FIGS. 6B and 6D and FIG. 7E the method is particularly useful for removing free nucleotides from the sample. As shown in FIG. 5 (lane 11), FIG. 6C and FIGS. 7B, 7C and 7D, protein impurities are also efficiently removed from the sample.

Example 3: RNA Purification Using Hydroxyapatite Chromatography

To test whether hydroxyapatite chromatography could be useful for the purification of large RNA, 80 µg of lithium chloride purified 10-kb RNA (replicon) from an in vitro transcription reaction were loaded on a hydroxyapatite column and eluted with a phosphate linear gradient composed of varying proportions of Buffer A (10 mM phosphate buffer, pH 6.8) and Buffer B (500 mM phosphate buffer, pH 6.8). It was found that mRNA can be efficiently bound and recovered from a hydroxyapatite column. RNA yield/recovery were measured by loading identical amounts of lithium chloride purified mRNA from an in vitro transcription reaction on a hydroxyapatite column or fed into the chromatography system by-passing the column. Area under the elution peaks was calculated and the ratio used as an indicator of RNA yield after column pass-through compared to without column pass-through purification (1401.25 mAu/ml vs 1934.76 mAu/ml). The RNA yield was calculated as 72%. Lithium chloride purified 10-kb RNA (replicon) from an in vitro transcription reaction was loaded on a hydroxyapatite column and eluted using phosphate buffer. Collected fractions 4, 5 and 6 were loaded on a denaturing RNA gel, confirming that the optical density read is associated with RNA.

To test whether RNA can be more efficiently separated from contaminants such as protein or non-digested DNA using hydroxyapatite chromatography, the elution dynamics of purified RNA were analysed in the presence of various amounts of a salt (0-1000 mM sodium chloride) in the elution buffer. Sodium chloride was added to both elution buffers A and B so to have a constant concentration throughout the phosphate gradient. The rightward shift of the RNA elution peak shows that an increasing concentration of phosphate is required for RNA elution with increasing salt concentrations. This allows for the setup of different conditions to further separate RNA from proteins or other impurities. The addition of salt to the phosphate elution buffer can therefore be exploited to optimise fractionation of RNA from impurities. It was found that mRNA yield is inversely related to the concentration of sodium chloride in the elution buffer.

To test whether RNA can be more efficiently separated from (undigested template) DNA, 100 µg of pure DNA or pure RNA were subjected to hydroxyapatite chromatography using the same parameters. A continuous gradient of a potassium phosphate elution buffer was used. Effect of elution conditions on separating DNA from RNA was determined. It was found that DNA is eluted at higher phosphate concentrations than RNA (rightward shift of the elution peak). The inventors therefore devised a step-wise elution method whereby the phosphate concentration in the elution buffer increases step-wise, rather than continuously. RNA can therefore be selectively eluted by choosing an elution buffer phosphate concentration at which RNA but not DNA or other contaminants are eluted. A test run was then performed where equal amounts of purified RNA and DNA were mixed to a total amount of 200 µg in solution and subjected to hydroxyapatite chromatography using a step-wise elution gradient of Buffer A and B.

In a gradient elution, RNA elution occurred at a buffer conductivity of around 21.04 mS/cm. DNA elution occurred at around 30.52 mS/cm. This demonstrates that in the presence of an RNA/DNA mixture, a concentration of about 180 mM potassium phosphate (or any potassium phosphate concentration resulting in a conductivity value above 21.04 mS/cm and below 30.52 mS/cm) elutes selectively RNA and not DNA. A test run was then performed where purified DNA was analysed under the same conditions as described above. No elution was observed below about 180 mM (~18% B) potassium phosphate. The results show that RNA and DNA can efficiently be separated with a step-wise elution. DNA elution can be achieved with 38% buffer B, about 380 mM potassium phosphate (or any potassium phosphate concentration resulting in a conductivity value above 30.52 mS/cm). Using tangential flow filtration and hydroxyapatite chromatography (in vitro transcription reaction sample), elution conditions for separating DNA from RNA were optimised.

Figure 2B:
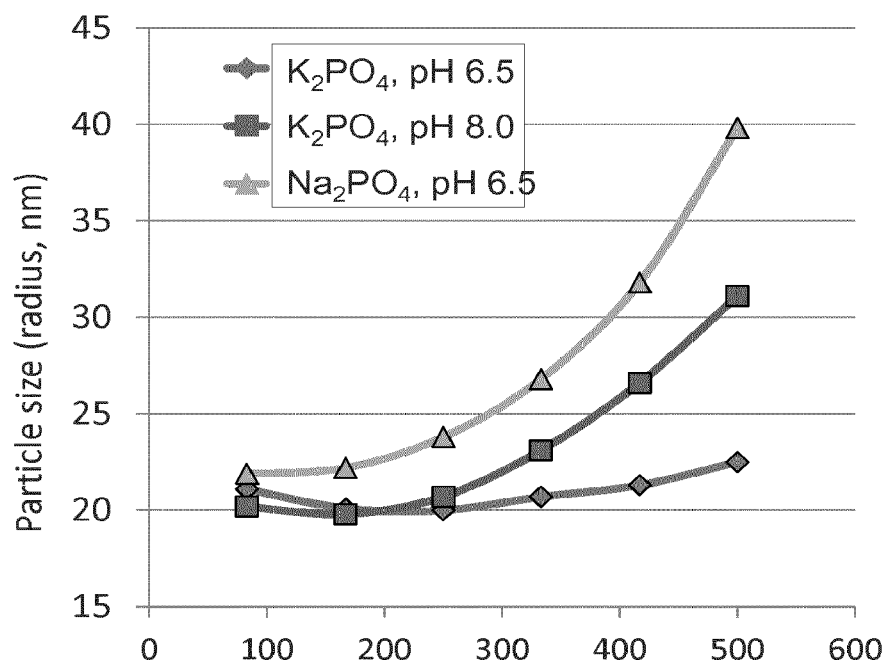

In comparing various phosphate buffers useful for elution of RNA during hydroxyapatite chromatography, it was found that a potassium phosphate buffer performs better than a sodium phosphate in keeping RNA in solution and is a better candidate for hydroxyapatite column elution. Dynamic light scattering experiments (FIG. 2) showed that an increasing concentration of sodium phosphate in the elution buffer during hydroxyapatite chromatography leads to an increasingly larger apparent particle size of the eluted RNA, probably due to salt-induced RNA precipitation ("salting out"). This effect is reduced when using potassium phosphate instead of sodium phosphate at the same concentration, with concentrations up to 500 mM. A potassium phosphate buffer was tested for RNA elution from a hydroxyapatite column and performed comparably to a sodium phosphate buffer in terms of RNA purity and recovery for this process. Potassium phosphate is therefore identified as the salt of choice for RNA purification by hydroxyapatite chromatography.

Next, a non-purified in vitro transcription reaction containing 100 μg of a 10-kb RNA replicon was analysed using hydroxyapatite chromatography. Collected fractions 1, 2 and 3 were loaded on a denaturing RNA gel. No RNA was visible on the gel. Fractions B9 (corresponding to fraction directly preceding fraction 2) and C1 (corresponding to fraction 3) were analysed by reversed phase HPLC. The elution time was compared to nucleotide standards, confirming that the observed elution peaks at OD 260 using a non-purified in vitro transcription reaction sample were mainly composed of free nucleotides from the in vitro transcription reaction.

Figure 3A:
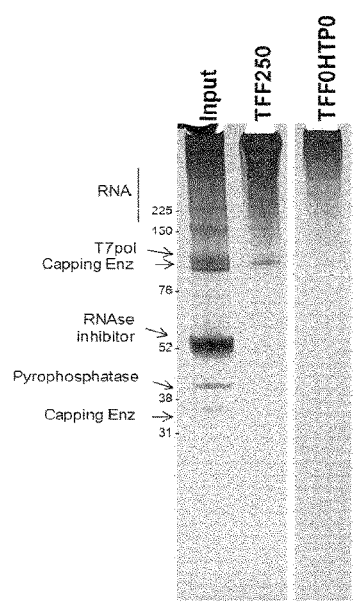
FIG. 3A shows the result of RNA purification using tangential flow filtration and hydroxyapatite chromatography: in vitro transcription reaction sample—protein removal—in vitro transcription reaction sample before purification (lane 1), after tangential flow purification (lane 2), after hydroxyapatite chromatography (lane 3).
Figure 3B:
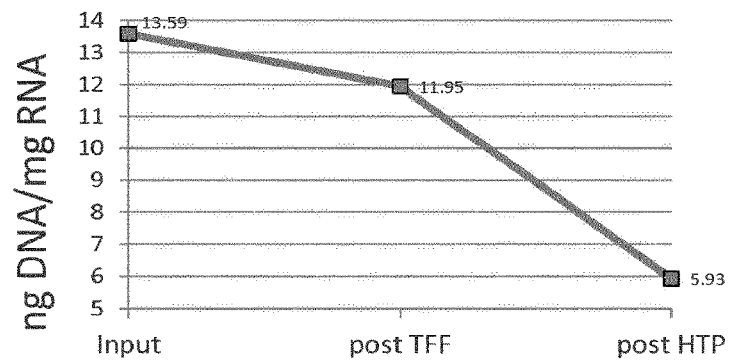
FIG. 3B shows the result of RNA purification using tangential flow filtration and hydroxyapatite chromatography: in vitro transcription reaction sample—DNA removal—DNA per mg of RNA present in an in vitro transcription reaction sample before purification (first data point from left), after tangential flow filtration (second data point), after hydroxyapatite chromatography (third data point).

Example 4: RNA Purification Using Tangential Flow Filtration and Hydroxyapatite Chromatography A combination of tangential flow filtration followed by hydroxyapatite chromatography was tested for improved efficiency of RNA purification from an in vitro transcription reaction sample, and in particular for the removal of nucleotides before the sample is used in hydroxyapatite chromatography. An unpurified in vitro transcription reaction containing a 10-kb RNA replicon product was used as the starting sample. FIGS. 3A and 3B show that such a combination of method allows the efficient removal of nucleotides in the tangential flow filtration step and of DNA (reduced to 5.93 ng DNA per mg purified RNA) and protein (reduced to below detection levels) in the hydroxyapatite chromatography step, enabling the recovery of pure RNA (>80%) after the hydroxyapatite chromatography step (a step-wise elution gradient as described in Example 3 was used for elution). This is particularly useful as template DNA digestion can be omitted from the overall RNA purification procedure, leading to faster operation times.

FIG. 1 further confirms the efficiency of protein removal using a hydroxyapatite chromatography step, showing that the level of protein impurities is reduced to below the level of detection using silver staining (4 μg of purified RNA were loaded per lane). An optional further step of tangential flow filtration was used to exchange the phosphate buffer in which the purified RNA is eluted following hydroxyapatite chromatography into a citrate buffer suitable for downstream applications.

FIG. 6C (lane "TFF0HTP0" vs. lane "Input") also confirms the usefulness of an RNA purification method combining tangential flow filtration followed by hydroxyapatite chromatography for removing protein impurities from an RNA-containing sample.

Example 5: RNA Purification Using Core Bead Flow-Through Chromatography

Figures 4A, 4B:
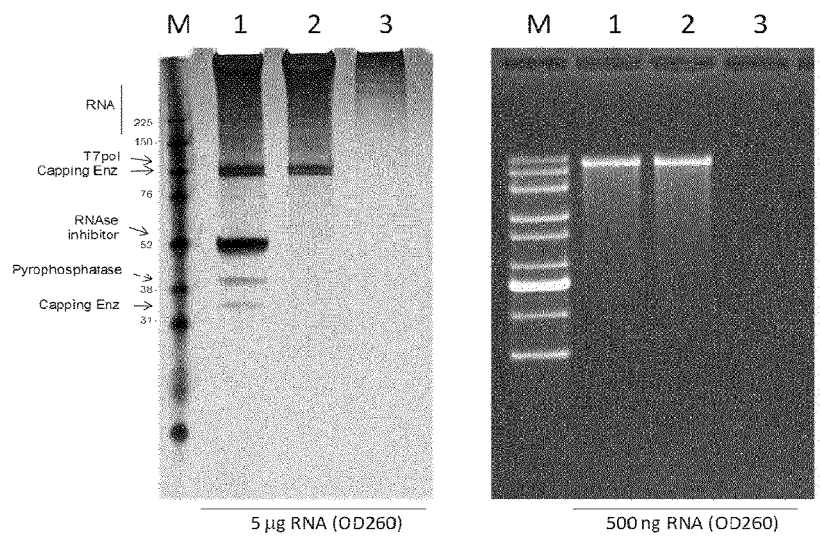
FIG. 4A-4B show the result of RNA purification using core bead flow-through chromatography: in vitro transcription reaction sample—protein removal—in vitro transcription sample before purification (lane 1), flow-through after core bead flow-through chromatography (lane 2), eluate after column cleaning-in-place (lane 3).

Core bead flow-through chromatography was tested for the purification of RNA. An unpurified in vitro transcription reaction (in Tris 50 mM, pH 8.0) containing a 10-kb RNA replicon product was used as the starting sample. A HiScreen Capto™ Core 700 column (product code: 17-5481-15) was initially used, on a GE ÄKTAa Explorer 100 FPLC system. The sample was diluted in a buffer of Tris 50 mM, pH 8.0, to a final RNA concentration of 600 ng/μl (final volume: 8.5 ml, containing 5.1 mg RNA). The sample was injected into the column and chased with Tris buffer (50 mM) until elution of the sample was complete. The flow was set at 1 ml/min (corresponding to 125 cm/h). Column cleaning-in-place (CIP) and regeneration was as per the manufacturer's instructions. It was found that RNA can be recovered in the column flow-through (e.g., in vitro transcription reaction sample, 5.1 mg RNA, RNA was eluted in flow through). FIGS. 4A and 4B show that RNA is recovered from the column flow-through at a high level of yield (FIG. 4B, lane 2 vs. lane 1) and contains lower levels of protein impurities compared to before core bead flow-through chromatography (FIG. 4A, lane 2 vs. lane 1).

To test the effect of the presence of salt on removal of protein impurities using core bead flow-through chromatography, increasing concentrations of sodium chloride or sodium phosphate added to the sample upon purification and in the chase buffer were tested. Chromatographic conditions for these purifications were equivalent to the ones specified above. Flow-through fractions containing an equal amount of purified RNA (5 μg) were analysed by polyacrylamide gel electrophoresis and silver staining. FIG. 5 shows that an increasing salt concentration positively correlates with the level of removal of proteinaceous contaminants. Salt was added to the sample and to the chase buffer. Arrows indicate two protein contaminants (T7 polymerase and large subunit of the capping enzyme). Control sample on the far right is after purification of an in vitro transcription reaction using tangential, flow filtration only. In conclusion, increasing salt, concentration facilitates the removal of protein carryover, leading to a final protein mass that is below the level of detection using a silver-stained polyacrylamide gel and 5 μg of RNA.

Figure 8:
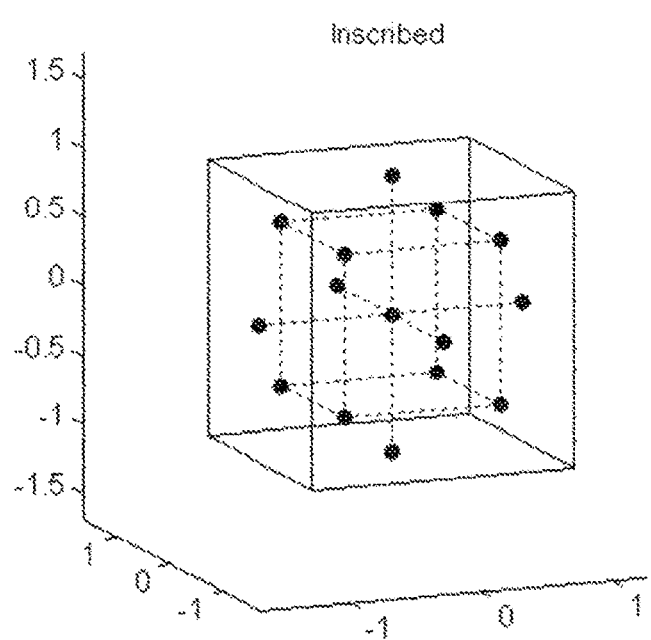
FIG. 8 shows the design of an experimental statistically significant approach for core bead flow-through chromatography—in vitro transcription reaction sample—optimisation of parameters—salt concentration: 0 mM (−1) to 500 mM (1); sample dilution: no dilution (1) to 4-fold dilution (−1); flow rate (linear velocity): 50 cm/h (−1) to 500 cm/h (1).

Conditions for core bead flow-through chromatography were further optimised, in particular the salt concentration (0-500 mM), flow rate (50-500 cm/h), and sample dilution (4-fold dilution to undiluted; before application to the column) were varied and evaluated for their effect on the level of RNA yield (recovery), protein removal (T7 polymerase and/or capping enzyme) and nucleotide removal after core bead flow-through chromatography and the pre-column pressure and operation time of the chromatography method. FIG. 8 shows the design of an experimental statistically significant approach. The value ranges for the tested variables and the output parameters that were evaluated are indicated. Model details: Response Surface Designs, Central Composite Designs, Inscribed. The starting sample was an unpurified in vitro transcription reaction sample containing the RNA of interest. Protein carryover was evaluated by silver-stained SDS page of the flow through material, and quantified by densitometry of the protein bands. Nucleotide removal and RNA yield were quantified as described in Example 1.

Table 1 shows the output values RNA yield (recovery), protein removal (T7 polymerase and capping enzyme), OD260 nm values, operation time and pre-column pressure after a core bead flow-through chromatography run under different conditions (samples A-T).

merase removal and capping enzyme removal; effect of flow rate and salt concentration on RNA recovery, T7 polymerase removal and capping enzyme removal.

Using an unpurified in vitro transcription reaction as the starting sample, the maximum sample volume per column volume (CV) was determined at which protein is sufficiently removed using core bead flow-through chromatography. Effect of sample-to-column volume ratio on protein removal

TABLE 1

| Samples | Inscribed CCI | | | Flow | | | Inj Vol | Inj RNA ug | ul on GEL |
|---|---|---|---|---|---|---|---|---|---|
| | Flow | Salt | Conc | cm/h | Salt mM | Conc | | | |
| A | −0.594 | −0.594 | −0.594 | 141.3 | 101.5 | 0.402 | 500 | 106.0 | 19.9 |
| B | 0.594 | −0.594 | −0.594 | 408.7 | 101.5 | 0.402 | 500 | 306.5 | 19.9 |
| C | −0.594 | 0.594 | −0.594 | 141.3 | 398.5 | 0.402 | 500 | 106.0 | 19.9 |
| D | 0.594 | 0.594 | −0.594 | 408.7 | 398.5 | 0.402 | 500 | 306.5 | 19.9 |
| E | −0.594 | −0.594 | 0.594 | 141.3 | 101.5 | 0.848 | 500 | 106.0 | 9.4 |
| F | 0.594 | −0.594 | 0.594 | 408.7 | 101.5 | 0.848 | 500 | 306.5 | 9.4 |
| G | −0.594 | 0.594 | 0.594 | 141.3 | 398.5 | 0.848 | 500 | 106.0 | 9.4 |
| H | 0.594 | 0.594 | 0.594 | 408.7 | 398.5 | 0.848 | 500 | 306.5 | 9.4 |
| I | 0.000 | 0.000 | 0.000 | 275.0 | 250.0 | 0.625 | 500 | 206.3 | 12.8 |
| L | 0.000 | 0.000 | 0.000 | 275.0 | 250.0 | 0.625 | 600 | 206.3 | 12.8 |
| M | 0.000 | 0.000 | 0.000 | 275.0 | 250.0 | 0.625 | 500 | 206.3 | 12.8 |
| N | 0.000 | 0.000 | 0.000 | 275.0 | 250.0 | 0.625 | 500 | 206.3 | 12.8 |
| O | 1.000 | 0.000 | 0.000 | 50.0 | 250.0 | 0.625 | 500 | 37.5 | 12.8 |
| P | 1.000 | 0.000 | 0.000 | 500.0 | 250.0 | 0.625 | 500 | 375.0 | 12.8 |
| Q | 0.000 | −1.000 | 0.000 | 275.0 | 0.0 | 0.625 | 500 | 206.3 | 12.8 |
| R | 0.000 | 1.000 | 0.000 | 275.0 | 500.0 | 0.625 | 500 | 206.3 | 12.8 |
| S | 0.000 | 0.000 | −1.000 | 275.0 | 250.0 | 0.250 | 500 | 206.3 | 32.0 |
| T | 0.000 | 0.000 | 1.000 | 275.0 | 250.0 | 1.000 | 500 | 206.3 | 8.0 |

| Samples | avg OD | | | Ribogreen | | | AU Protein | Flow through Time | Pre column Pressure |
|---|---|---|---|---|---|---|---|---|---|
| | ng/ul | total | recovery % | ng/ul | total | recovery % | | | |
| A | 91.9 | 229.6 | 95.2 | 112.8 | 281.9 | 116.8 | 0.162 | 0.0176 | 0.140 |
| B | 103.9 | 259.6 | 107.6 | 119.3 | 298.2 | 123.6 | 0.297 | 0.0061 | 0.260 |
| C | 131.0 | 327.5 | 135.7 | 105.1 | 262.8 | 108.9 | 0.083 | 0.0176 | 0.140 |
| D | 142.9 | 357.1 | 148.0 | 102.3 | 255.7 | 106.0 | 0.100 | 0.0061 | 0.260 |
| E | 227.7 | 569.3 | 111.9 | 214.8 | 537.1 | 105.6 | 0.221 | 0.0083 | 0.160 |
| F | 254.8 | 636.9 | 125.2 | 237.4 | 593.5 | 116.7 | 0.221 | 0.0029 | 0.260 |
| G | 259.6 | 648.9 | 127.6 | 183.2 | 458.0 | 90.0 | 0.080 | 0.0083 | 0.160 |
| H | 291.1 | 727.8 | 143.1 | 202.4 | 506.1 | 99.5 | 0.122 | 0.0029 | 0.280 |
| I | 204.0 | 509.9 | 136.0 | 198.5 | 496.2 | 132.3 | 0.160 | 0.0058 | 0.200 |
| L | 206.1 | 515.1 | 137.4 | 191.6 | 479.0 | 127.7 | 0.169 | 0.0058 | 0.200 |
| M | 206.4 | 516.0 | 137.6 | 160.7 | 401.6 | 107.1 | 0.144 | 0.0058 | 0.200 |
| N | 211.8 | 529.5 | 141.2 | 174.3 | 435.7 | 116.2 | 0.104 | 0.0058 | 0.200 |
| O | 180.8 | 452.0 | 120.5 | 157.7 | 394.1 | 105.1 | 0.062 | 0.0320 | 0.070 |
| P | 210.7 | 526.8 | 140.5 | 197.7 | 494.3 | 131.8 | 0.112 | 0.0032 | 0.320 |
| Q | 140.3 | 350.6 | 93.5 | 178.1 | 445.1 | 118.7 | 0.156 | 0.0058 | 0.210 |
| R | 208.2 | 520.4 | 138.8 | 142.1 | 355.2 | 94.7 | 0.064 | 0.0058 | 0.200 |
| S | 72.0 | 180.0 | 120.0 | 76.4 | 190.9 | 127.3 | 0.018 | 0.0145 | 0.200 |
| T | 315.9 | 789.8 | 131.6 | 269.6 | 674.1 | 112.3 | 0.096 | 0.0036 | 0.200 |

The output parameters T7 polymerase removal and capping enzyme removal in samples A-T were quantified by resolution of the core bead chromatography flow through fraction using polyacrylamide gel electrophoresis and silver-stained followed by quantification using densitometry of the protein bands. An unpurified in vitro transcription sample was used as control. Results were further analysed according to chromatography conditions: effect of salt concentration and sample dilution on RNA recovery, T7 polymerase removal (quantification in relative units) and capping enzyme removal (quantification in relative units); effect of flow rate and sample dilution on RNA recovery, T7 polywas determined. Samples were diluted up to a maximum sample/CV ratio of 10:1 (CV: 1 ml; ID: 0.7 cm; height: 2.5 cm, L. vel: 250 cm/h; flow: 1.6 ml/min; contact time: 36 seconds) or 64:1 (CV: 0.137 ml; ID: 0.5 cm; height: 0.7 cm, L. vel: 250 cm/h; flow: 0.82 ml/min; contact time: 10 seconds) and potassium chloride was added to a final concentration of 250 mM. The flow-through from each run was analysed by polyacrylamide gel electrophoresis and silver staining. It was found that protein break-through occurred when the sample-CV ratio exceeded about 10:1, under the conditions used. In conclusion, a sample/CV ratio of up to 10 efficiently purified RNA from protein impurities in the experimental condition used (e.g. 10 ml IVT reaction can be diluted to 40 ml and efficiently purified with a 1 ml column).

Further, various sample and/or chase buffers compositions for use in core bead flow-through chromatography were compared with regards to the degree of observed RNA precipitation in these buffers, measured using dynamic light scattering and an increasing apparent particle size as an indicator of RNA precipitation. Table 2 summarizes the results of core bead flow-through chromatography: dynamic light scattering analysis of RNA aggregate particle size in the presence of various salts. The second column refers to salt concentration in mM. Numbers in columns 3-7 are particle radius in nm. The Table shows that potassium phosphate buffer (pH 6.5) and potassium chloride buffer (pH 8.0) are good candidates for an optimised flow through purification.

TABLE 2

|  |  | Tris 10 mM pH 8.0 + NaCl | Tris 10 mM pH 8.0 + KCl | KPO4 pH 6.5 | KPO4 pH 8.0 | NaPO4 pH 6.5 |
|---|---|---|---|---|---|---|
| NaCl | 0 | 20.3 |  |  |  |  |
| (mM) | 83 | 23.2 | 22.3 | 21.1 | 20.2 | 21.9 |
|  | 167 | 21.8 | 20.4 | 20.1 | 19.8 | 22.2 |
|  | 250 | 22 | 19.7 | 20 | 20.7 | 23.8 |
|  | 333 | 23.9 | 19.4 | 20.7 | 23.1 | 26.8 |
|  | 417 | 27.6 | 20.2 | 21.3 | 26.6 | 31.8 |
|  | 500 | 32.6 | 21.3 | 22.5 | 31.1 | 39.8 |

Example 6: RNA Purification Using Core Bead Flow-Through Chromatography and Tangential Flow Filtration Using an unpurified in vitro transcription reaction as the starting sample containing a 10-kb RNA replicon product, nucleotide and protein removal were compared using either tangential flow filtration or core bead flow-through chromatography (using potassium chloride concentrations of 0, 250 or 500 mM in the sample). FIGS. 6B and 6D show that tangential flow filtration efficiently removes nucleotide impurities. FIG. 6C shows that core bead flow-through chromatography efficiently removes protein impurities in the presence of potassium chloride. Therefore, where it is desired to remove nucleotide and protein impurities, it is desired that core bead flow-through chromatography is followed by tangential flow filtration.

Example 7: RNA Purification Using Core Bead Flow-Through Chromatography and Hydroxyapatite Chromatography The presence of additional salts such as potassium chloride in the sample and/or chase buffer may sometimes be undesired. Using an unpurified in vitro transcription reaction as the starting sample containing a 10-kb RNA replicon, protein removal was compared using core bead flow-through chromatography (without additional salt, i.e. 0 mM potassium chloride) alone or followed by hydroxyapatite chromatography (also without additional salt, i.e. 0 mM sodium chloride). FIG. 6C (lane "CC0HTP0" vs. lane "CC0") shows that efficient protein removal can be achieved even in the absence of additional salt, when core bead flow-through chromatography is followed by hydroxyapatite chromatography.

Example 8: Combinations of Methods for RNA Purification and Buffer Exchange

Four different process streams (P1-P4) were devised for RNA purification (Table 3) and compared with regards to RNA recovery/yield and purity (FIGS. 6A-6G).

TABLE 3

| | Process stream | | |
|---|---|---|---|
| Options: | Purification | → | Buffer Exchange |
| 1 | TFF (puri b.) | → | TFF (formulation b.) |
| 2 | TFF (no salts) → LC (hydroxyhapatite) | → | TFF (formulation b.) |
| 3 | GE Core beads (250 KCl) | → | TFF (formulation b.)/SEC |

TABLE 3-continued

| | Process stream | | |
|---|---|---|---|
| Options: | Purification | → | Buffer Exchange |
| 4 | GE Core beads (no salts) → LC (hydroxyhapatite) | → | TFF (formulation b.) |

An in vitro reaction containing a 10-kb RNA replicon of interest was used as the starting sample.

RNA purity was related to the level of protein (T7 polymerase, capping enzyme, RNase inhibitor, pyrophosphatase, *E. coli* proteins carried over from DNA template amplification), plasmid DNA and nucleotide after each step. RNA recovery and nucleotide levels were measured using the methods of Example 1. Protein levels were measured using ELISA or polyacryl amid gel electrophoresis followed by silver staining or antibody-based detection (western blot). DNA levels were measured by quantitative PCR.

A step of tangential flow filtration can be used to exchange buffer but where this results in increased purity it is also a purification step.

For purposes of comparison, a step of DNA digestion using DNase was performed for all processes after IVT and before applying the sample to the chromatography/filtration system. However, it should be noted that this step is not mandatory for example where hydroxyapatite chromatography is used.

FIGS. 7A-7G show that protein carryover (T7 and capping enzyme) is observed only with process 1. Hydroxyapatite chromatography and core bead chromatography can remove protein carry over efficiently. Traces are detected after purification, below the level of detection of the ELISA assay. Core bead flow-through purification followed by tangential flow filtration is easier to operate that hydroxyapatite chromatography. RNA yield was: P1: 74.8%, P2:

37.3%, P3: 76.2%, P4: 60.7% (RNA recovery is summarized in Table 4). Nucleotide removal was complete in all processes in the final product. Process time ranges from 45 mins to 84 mins for all processes. DNA concentration in the final product was 0.6 ng DNA per 75 µg RNA. The level of E. coli protein contamination was below the detection level of the western blot method used. The apparent RNA particle size as measured by dynamic light scattering in the final product was 40-45 nm radius for all processes.

TABLE 4

|    | Step:       | Step recovery | Overall recovery |
|----|-------------|---------------|------------------|
| P1 | 1 - TFF250  | 13.8          |                  |
|    | 2 - TFFfb   | 543.4         | 74.8             |
| P2 | 1 - TFF0    | 81.9          |                  |
|    | 2 - HTP0    | 77.0          | 63.0             |
|    | 3 - TFFfb   | 59.2          | 37.3             |
| P3 | 1 - CC250   | 88.7          |                  |
|    | 2 - TFFfb   | 85.9          | 76.2             |
| P4 | 1 - CC0     | 90.1          |                  |
|    | 2 - HTP0    | 88.8          | 79.9             |
|    | 3 - TFFfb   | 75.9          | 60.7             |

Example 9: Large-Scale Purification of RNA

A combination of tangential flow filtration followed by hydroxyapatite chromatography was used for preparative RNA purification from an in vitro transcription reaction sample. An unpurified in vitro transcription reaction containing 6 mg of a 10-kb RNA capped replicon product was used as the starting sample. Tangential flow filtration was performed using 10 mM Tris pH 8.0. The RNA-containing fraction was retained. Potassium chloride was added to the sample at a final concentration of 500 mM, and the sample was applied to the hydroxyapatite column (CHT™ Ceramic Hydroxyapatite Type II, 40 µm particle size, Biorad, in a GE Hi Scale 26 column, 20 cm height, 100 ml; run on a GE ÄKTA explorer 100; flow 10 ml/min; linear velocity 300 cm/h). Elution buffers were buffer A (10 mM potassium phosphate, pH 6.5) and buffer B (1M potassium phosphate, pH 6.5). RNA was selectively eluted with 18% buffer B (180 mM potassium phosphate). The results demonstrate that this method achieves large-scale, preparative RNA purification with high yield and purity.

A combination of core bead flow-through chromatography followed by TFF was used for preparative RNA purification from an in vitro transcription reaction sample. An unpurified in vitro transcription reaction containing 120 mg of a 10-kb capped RNA replicon product was used as the starting sample. The sample was, diluted 4-fold, then potassium chloride to 250 or 500 mM was optionally added, and the sample was applied to a core bead flow-through column using Capto™ Core 700 beads. Chromatography was performed at a linear flow rate of 275 cm/h (volumetric 25 ml/min) with a contact time of 2.21'. The RNA-containing flow-through was then further purified, concentrated 2-fold, and buffer-exchanged into final formulation buffer (all in one procedure) using TFF (hollow-fibre module, 500 kDa cut-off, mPES).

The process was tested with 100 ml capped IVT RNA (about 120 mg), using a 50 ml Captocore column (Captocore 700, 2.6 cm internal diameter, 10 cm height run at the conditions described above, flow 25 ml/min) and a 790 cm 2 TFF cartridge (same conditions, flow 200 ml/min). The final material had comparable characteristics to the smaller scale process in terms of activity, purity and yield. Even in preliminary experiments the process had a yield of about 80% per step, giving a recovery of 65% overall, and was completed in 70' (12 minutes for the Captocore step, 58 minutes for TFF).

The following table shows suitable process parameters for four available columns which can cope with sample volumes of from 10 to 1000 ml:

|                     | sample Volume (ml) | Linear velocity (cm/h) | Contact time (min) | Internal diameter (cm) | Area (cm2) | Height (cm) | Column volume (ml) | Sample/ CV | Dilution final volume (ml) | Flow (ml/min) | Process time (min) |
|---------------------|--------------------|------------------------|--------------------|------------------------|------------|-------------|--------------------|------------|----------------------------|---------------|--------------------|
| GE HiScreen         | 10                 | 275                    | 2.21               | 0.77                   | 0.47       | 10.13       | 4.71               | 2.32       | 40                         | 2.1           | 19                 |
| GE HiScale 26/20    | 100                | 275                    | 2.21               | 2.60                   | 5.31       | 10.13       | 53.75              | 1.86       | 400                        | 24.3          | 16                 |
| GE HiScale 26/20    | 200                | 275                    | 2.21               | 2.60                   | 5.31       | 10.13       | 53.75              | 3.72       | 800                        | 24.3          | 33                 |
| Spectra/Chrom 50/100| 1000               | 275                    | 2.21               | 5.00                   | 19.63      | 10.13       | 198.78             | 5.03       | 4000                       | 89.9          | 44                 |

The table shows flow rate as a linear velocity, which means that the columns' internal diameters are irrelevant in defining the in method. Linear velocity can be maintained constant in the scaled-up processes. The different column diameter is used to calculate the flow rate in so as to keep the linear velocity constant and thus to maintain the same contact time (i.e. the time that the sample stays in the column).

REFERENCES

Andrews-Pfannkoch et al. Appl Environ Microbiol. 2010; 76(15):5039-5045.
Beland et al. J Chromatogr. 1979; 174(1):177-186.
Bernardi. Nature. 1965; 206:779-783.
Eon-Duval et al. Anal Biochem. 2003; 316(1):66-73.
Gennaro, 2000, Remington: The Science and Practice of Pharmacy. 20th edition, ISBN: 0683306472
Guerrero-German et al. Bioprocess Biosyst Eng. 2009; 32(5):615-623.
Kahn et al. Biotechnol Bioeng. 2000; 69(1):101-106.
Kamalay et al. Proc Natl Acad Sci USA. 1984; 81(9):2801-2805.
Kendall et al. Biotechnol Bioeng. 2002; 79(7):816-822.
Lovdal et al. Dis Aquat Organ. 2002; 49(2):123-128.
Pascolo S. Methods Mol Med. 2006; 127:23-40.
Zhang et al. PLOS Biol. 2006; 4(1):108-118.

The invention claimed is:
1. A method for removing protein contaminants from a desired RNA species in an RNA-containing sample, said method comprising the steps of:

removing the protein contaminants from said desired RNA species in said RNA containing sample by applying said RNA-containing sample to a core bead flow-through chromatography medium comprising porous beads having a molecular weight cut-off (MWCO)/pore size of at least 250 kDa, wherein said RNA-containing sample comprises an in vitro transcription reaction sample; and obtaining an RNA-containing sample without the protein contaminants from a flow-through of said core bead flow-through chromatography medium, wherein said protein contaminants are in a size that can enter pores in said porous beads and said desired RNA-containing species has a molecular weight cut-off/pore size that is larger than the molecular weight cut-off/pore size of the porous beads.

2. The method of claim 1, wherein the molecular weight cut-off (MWCO)/pore size of at least 250 kDa is a molecular weight cut-off/pore size of at least 300 kDa.

3. The method according to claim 1, wherein the desired RNA species is a single-stranded RNA.

4. The method according to claim 3, wherein the single-stranded RNA is an mRNA.

5. The method according to claim 3, wherein the single-stranded RNA comprises one or more nucleotides having a modified nucleobase.

6. The method according to claim 1, wherein the desired RNA species comprises a linear sequence of at least 2,000 nucleotides.

7. The method according to claim 1, wherein a salt is added to the RNA-containing sample to a final concentration between 0 mM and 500 mM.

8. The method according to claim 1, wherein the method further comprises preparing said RNA-containing sample by pre-purifying an in vitro transcription reaction sample.

9. The method according to claim 1, wherein the method is conducted using a buffer containing a potassium salt.

10. The method according to claim 1, wherein the desired RNA species obtained from the method is purified to a preparative scale.

11. The method according to claim 1, wherein the method further includes discarding materials which do not contain the desired RNA species from the RNA-containing sample.

12. The method according to claim 1, wherein the RNA-containing sample contains one or more of: plasmid DNA, deoxy-oligonucleotides, deoxynucleoside monophosphates, ribonucleoside triphosphates and proteins; and wherein the RNA-containing sample does not contain genomic DNA and/or a cell membrane or fragments thereof.

13. The method according to claim 1, wherein the RNA-containing sample contains the RNA species and plasmid DNA, deoxy-oligonucleotides, deoxynucleoside monophosphates, ribonucleoside triphosphates and proteins.

14. The method according to claim 1, wherein the desired RNA species comprises a linear sequence of at least 1,000 nucleotides.

15. The method according to claim 1, further comprises purification of said desired RNA species.

16. The method according to claim 15, wherein the purification step is conducted using tangential flow filtration.

17. The method according to claim 16, wherein the tangential flow filtration is a tangential flow filtration system having a hydrophilic membrane.

18. The method according to claim 1, wherein the in vitro transcription sample is made by an in vitro transcription of an RNA.

19. The method according to claim 1, wherein the desired RNA species obtained from the method is at least 99% pure.

20. The method according to claim 1, wherein the desired RNA species obtained from the method is free from DNA, pyrophosphates, and nucleotides.

21. The method according to claim 1, further comprises purifying the RNA-containing sample without the protein contaminants using a tangential flow filtration system.

22. The method according to claim 21, wherein said purifying the RNA-containing sample without the protein contaminants using a tangential flow filtration system is performed immediately after the obtaining step.

23. The method according to claim 1, wherein the cores of said porous beads are bound with a ligand with multiple functionalities.

24. The method according to claim 23, wherein the ligand is both hydrophobic and positively charged.

25. The method according to claim 1, wherein the core bead flow-through chromatography medium is a core bead flow-through chromatography column.

26. The method of claim 1, wherein the molecular weight cut-off (MWCO)/pore size of at least 250 kDa is a molecular weight cut-off/pore size of-at least about 700 kDa.

27. A method for preparing a pharmaceutical composition comprising a purified desired RNA species, comprising the steps of:

(a) removing protein contaminants from a desired RNA species in an RNA-containing sample by applying said RNA-containing sample to a core bead flow-through chromatography medium comprising porous beads having a molecular weight cut-off (MWCO)/pore size of at least 250 kDa, wherein said RNA-containing sample comprises an in vitro transcription reaction sample, wherein said protein contaminants are in a size that can enter pores in said porous beads and said desired RNA-containing species has a molecular weight cut-off/pore size that is larger than the molecular weight cut-off/pore size of the porous beads;

(b) obtaining a purified RNA-containing sample comprising said purified desired RNA species from a flow-through of said core bead flow-through chromatography medium; and (c) preparing said pharmaceutical composition by formulating said purified desired RNA species from the purified RNA-containing sample to form a pharmaceutical composition.

28. The method of claim 27, wherein said method removes undesired components comprising nucleotides from said RNA-containing sample.

29. The method according to claim 27, wherein said method further comprises purification of said purified RNA-containing sample using a hydroxyapatite chromatography.

30. The method according to claim 27, wherein said method further comprises purification of said purified RNA-containing sample using a tangential flow filtration system.

31. The method of claim 27, wherein the molecular weight cut-off (MWCO)/pore size of at least 250 kDa is a molecular weight cut-off/pore size of at least about 700 kDa.

32. The method according to claim 27, wherein said method for further comprises purification of the RNA-containing sample without the protein contaminants using a tangential flow filtration system.

33. A method for removing protein contaminants from a desired RNA species in an RNA-containing sample, said method comprising the steps of:

removing the protein contaminants from said desired RNA species in said RNA containing sample by applying said RNA-containing sample to a core bead flow-through chromatography column having a stationary phase comprising porous beads having a molecular weight cut-off (MWCO)/pore size of at least 250 kDa, wherein said RNA-containing sample comprises an in vitro transcription reaction sample; and obtaining an RNA-containing sample without the protein contaminants from a flow-through of said core bead flow-through chromatography column, wherein said protein contaminants are in a size that can enter pores in said porous beads and said desired RNA-containing species has a molecular weight cut-off/pore size that is larger than the molecular weight cut-off/pore size of the porous beads.

34. The method of claim 33, wherein the molecular weight cut-off (MWCO)/pore size of at least 250 kDa is a molecular weight cut-off/pore size of at least 600 kDa.

35. The method of claim 33, wherein the molecular weight cut-off (MWCO)/pore size of at least 250 kDa is a molecular weight cut-off/pore size of at least about 700 kDa.

36. The method according to claim 35, wherein the cores of said porous beads are bound with a ligand with multiple functionalities.

37. The method according to claim 36, wherein the ligand is both hydrophobic and positively charged.

38. The method according to claim 35, wherein said method further comprises purification of the RNA-containing sample without the protein contaminants using a hydroxyapatite chromatography.

* * * * *